US011229625B2

(12) United States Patent
Wang et al.

(10) Patent No.: US 11,229,625 B2
(45) Date of Patent: Jan. 25, 2022

(54) TITRATION OF CEBRANOPADOL

(71) Applicant: GRÜNENTHAL GMBH, Aachen (DE)

(72) Inventors: Shaonan Wang, Mühltal/Traisa (DE); Chiara Piana, Florence (IT); Roberta Bursi, Den Bosch (NL)

(73) Assignee: PARK THERAPEUTICS, INC., Monmouth Junction, NJ (US)

( * ) Notice: Subject to any disclaimer, the term of this patent is extended or adjusted under 35 U.S.C. 154(b) by 0 days.

(21) Appl. No.: 16/116,055

(22) Filed: Aug. 29, 2018

(65) Prior Publication Data

US 2018/0369199 A1 Dec. 27, 2018

Related U.S. Application Data

(63) Continuation of application No. PCT/EP2017/025034, filed on Feb. 28, 2017.

(30) Foreign Application Priority Data

Feb. 29, 2016 (EP) ...................................... 16157868
Aug. 11, 2016 (EP) ...................................... 16020302

(51) Int. Cl.
*A61K 31/407* (2006.01)
*A61P 29/00* (2006.01)

(52) U.S. Cl.
CPC ............ *A61K 31/407* (2013.01); *A61P 29/00* (2018.01)

(58) Field of Classification Search
CPC .............................. A61K 31/407; A61P 29/00
See application file for complete search history.

(56) References Cited

U.S. PATENT DOCUMENTS 6,339,105 B1 1/2002 Karnin et al.
7,547,707 B2 6/2009 Hinze et al.
(Continued)

FOREIGN PATENT DOCUMENTS

EP 1 985 292 A1 10/2008
WO 00 25769 A1 5/2000
(Continued)

OTHER PUBLICATIONS

Salat et al., Cebranopadol: a first-in-class potent analgesic agent with agonistic activity at nociceptin/orphanin FQ and opioid receptors, 2015, Expert. Opin. Investig. Drug, 24(6), pp. 837-844 (Year: 2015).*

(Continued)

*Primary Examiner* — Savitha M Rao
(74) *Attorney, Agent, or Firm* — Norris McLaughlin, P.A.

(57) ABSTRACT

The invention relates to Cebranopadol for use in the treatment of pain, wherein Cebranopadol is administered according to an administration regimen comprising
(i) a first administration interval, which lasts for at least 2 consecutive days, wherein a first daily dose of Cebranopadol is administered on every day of the first administration interval; and
(ii) a second administration interval, which lasts for at least 2 consecutive days and directly follows the first administration interval without interruption, wherein a second daily dose of Cebranopadol is administered on every day of the second administration interval;
wherein the first daily dose of Cebranopadol is lower than the second daily dose of Cebranopadol.

50 Claims, 11 Drawing Sheets

(56) References Cited

U.S. PATENT DOCUMENTS

| | | |
|---|---|---|
| 7,799,931 B2 | 9/2010 | Hinze et al. |
| 7,951,948 B2 | 5/2011 | Hinze et al. |
| 8,053,576 B2 | 11/2011 | Hinze et al. |
| 9,120,797 B2 | 9/2015 | Hinze et al. |
| 9,862,719 B2 | 1/2018 | Hinze et al. |
| 2006/0004034 A1 | 1/2006 | Hinze et al. |
| 2008/0125475 A1 | 5/2008 | Hinze et al. |
| 2009/0156626 A1 | 6/2009 | Hinze et al. |
| 2009/0163716 A1 | 6/2009 | Hinze et al. |
| 2010/0240897 A1 | 9/2010 | Hinze et al. |
| 2011/0015220 A1 | 1/2011 | Linz et al. |
| 2011/0319440 A1 | 12/2011 | Hinze et al. |
| 2015/0322080 A1 | 11/2015 | Hinze et al. |
| 2015/0342929 A1 | 12/2015 | Linz et al. |

FOREIGN PATENT DOCUMENTS

| | | |
|---|---|---|
| WO | 2004 043967 A1 | 5/2004 |
| WO | 2008 040481 A1 | 4/2008 |
| WO | 2012 016695 A2 | 2/2012 |
| WO | 2012 016697 A2 | 2/2012 |
| WO | 2012 016698 A2 | 2/2012 |
| WO | 2012 016699 A2 | 2/2012 |
| WO | 2012 016703 A2 | 2/2012 |
| WO | 2013 007361 A1 | 1/2013 |

OTHER PUBLICATIONS

Coluzzi et al., Good clinical practice guide for opioids in pain management: the three Ts—titration (trial), tweaking (tailoring), transition (tapering), 2016 (available online 2014), Rev Bras Anestesiol, 66(3), pp. 310-317 (Year: 2014).*

Skaer, "Transdermal opioids for cancer pain", Health and Quality of Life Outcomes, 4: 1-9 (2006).

Klepstad, et al., "Starting Step III opioids for moderate to severe pain in cancer patients: Dose titration: A systematic review" Palliative Medicine, 25(5): 424-430 (2010).

Dowell, CDC Guideline for Prescribing Opioids for Chronic Pain, Recommendations and Reports, 65(1): 1-50 (2016).

Nuckols, Ann. et al., "Opioid Prescribing: A Systematic Review and Critical Appraisal of Guidlines for Chronic Pain"; Intern. Med., 160(1): 38-47 (2014).

* cited by examiner

TITRATION OF CEBRANOPADOL

PRIORITY CLAIM

This application is a continuation of International Patent Application No. PCT/EP2017/025034, filed Feb. 28, 2017, which, in turn, claims priority of European Patent Application No. 16020302.2, filed Aug. 11, 2016, and European Patent Application No. 16157868.7, filed Feb. 29, 2016, the contents of which patent applications are hereby incorporated herein by reference.

FIELD OF THE INVENTION

The invention relates to an administration regimen for the administration of the analgesic Cebranopadol. The administration regimen achieves the desired analgesic effect while reducing the probability of incidence of side effects.

BACKGROUND OF THE INVENTION

Cebranopadol (trans-6'-fluoro-4',9'-dihydro-N,N-dimethyl-4-phenyl-spiro[cyclohexane-1,1'-(3'H)-pyrano[3,4-b]indol]-4-amine) is an analgesic nociceptin/orphanin FQ peptide (NOP) and opioid receptor agonist (WO 2004/043967, WO 2008/040481, WO 2012/016703, WO 2012/016699, WO 2012/016695, WO 2012/016698, WO 2012/016697, WO 2013/007361).

Cebranopadol exhibits highly potent and efficacious antinociceptive and antihypersensitive effects in several rat models of acute and chronic pain with $ED_{50}$ values of 0.5-5.6 µg/kg after intravenous and 25.1 µg/kg after oral administration. In comparison with selective MOP receptor agonists, Cebranopadol was more potent in models of chronic neuropathic than acute nociceptive pain.

To characterize the side effect profile of Cebranopadol, safety pharmacology studies were carried out in rats. These studies focused on typical opioid-type side effects within the CNS and the respiratory system. Cebranopadol displays broad activity in various pain states and is highly potent and efficacious in animal models of acute nociceptive, inflammatory, cancer, and, especially, chronic neuropathic pain. In contrast to opioids such as Morphine, Cebranopadol displays higher analgesic potency in chronic pain, especially of neuropathic origin, than in acute nociceptive pain. In addition, even after doses higher than those required for inducing analgesia, Cebranopadol affects neither motor coordination nor respiratory function and thus displays a better tolerability profile than opioids. As a result, there is a broader therapeutic window for Cebranopadol than for Morphine (K. Linz et al., J. Pharmacol. Exp. Ther. 2014 535-548).

Cebranopadol is well tolerated. However, clinical trials revealed that treatment emergent adverse events can occur which may lead to early discontinuation of the treatment. The most frequently reported adverse events observed in clinical trials of Cebranopadol are associated with the central nervous system (e.g. dizziness) and the gastrointestinal tract (e.g. nausea and vomiting).

Various concepts to decrease the occurrence of adverse side effects (treatment emergent adverse events, TEAE) are known in the prior art. For example, eating and drinking habits, drug formulations, release kinetics, and/or the route of administration can be changed. Drug targeting may also be considered. Further, a second drug can be co-administered simultaneously with, before or after the drug of interest in order to suppress its adverse side-effects.

However, these measures can impair patient compliance by, for example, forcing the patient to change his habitual life style. Further, changing the mode of administration, e.g. from oral to rectal, is conceived by many patients as uncomfortable and unhygienic. The resulting decreased patient compliance can result in termination of a required drug therapy.

It is an object of the invention to improve the tolerability of Cebranopadol in the treatment of pain, preferably of chronic pain, particularly to reduce the frequency of dizziness, nausea and vomiting without diminishing the analgesic efficacy and the patient compliance.

This object has been achieved by the subject-matter of the patent claims.

SUMMARY OF THE INVENTION

A first aspect of the invention relates to Cebranopadol for use in the treatment of pain, wherein Cebranopadol is administered according to an administration regimen comprising
(i) a first administration interval, which lasts for at least 1 day, preferably for at least 2 consecutive days, wherein a first daily dose of Cebranopadol is administered on every day of the first administration interval; and
(ii) a second administration interval, which lasts for at least 1 day, preferably for at least 2 consecutive days and directly follows the first administration interval without interruption, wherein a second daily dose of Cebranopadol is administered on every day of the second administration interval;
wherein the first daily dose of Cebranopadol is lower than the second daily dose of Cebranopadol.

The administration regimen is preferably divided into a titration phase which is directly followed by a continuous phase without interruption.

During the titration phase, the administered daily dose of Cebranopadol is altered from time to time. Preferably, an unaltered, i.e. constant dose of Cebranopadol is administered for several days, e.g. for 3 days, for 4 days, for 5 days, for 6 days, or for 7 days, and after said several days the dose of Cebranopadol is altered, preferably increased, and then said altered dose of Cebranopadol is administered for another several days, e.g. for another 3 days, for another 4 days, for another 5 days, for another 6 days, or for another 7 days during which the dose of Cebranopadol is kept constant again. Thus, the titration phase typically involves administration of daily doses that are altered incrementally, whereas the time spans between consecutive increments typically last more than 1 day.

Accordingly, the titration phase preferably comprises administration intervals which consecutively follow one another. During the consecutive day(s) of a first administration interval, first daily dose of Cebranopadol is administered on every day, whereas during the consecutive day(s) of a second administration interval, which directly follows the first administration interval without interruption, second daily dose of Cebranopadol is administered on every day. Thus, alteration of dose occurs between the first administration interval and the second administration interval, whereas during the first administration interval on the one hand and during the second administration interval on the other hand the administered daily dose of Cebranopadol is kept constant independently of one another.

Preferably, the titration phase encompasses at least 2 administration intervals, preferably 3 or 4 or 5 or 6 or 7 or more administration intervals, at which different daily doses of Cebranopadol are administered, preferably once daily (sid), preferably orally, resulting in biphasic, triphasic, tetraphasic, pentaphasic, hexaphasic, heptaphasic and further multiphasic regimens, respectively.

The continuous phase of the administration regimen directly follows the titration phase without interruption. Typically, the daily dose of Cebranopadol that is administered during the last administration interval of the titration phase corresponds to the daily dose of Cebranopadol that is consecutively and constantly administered during the continuous phase. Thus, in this regard the duration of the last administration interval of the titration phase is not particularly limited, as said last administration interval is typically followed by the continuous phase without a further change of the daily dose of Cebranopadol.

Preferably, the titration phase of the administration regimen comprises at least 1, at least 2, at least 3, at least 4, at least 5, at least 6, or at least 7 days, more preferably at least 8, at least 9, at least 10, at least 11, at least 12, at least 13, or at least 14 days, still more preferably at least 15, at least 16, at least 17, at least 18, at least 19, at least 20, or at least 21 days.

It has been surprisingly found that initiating Cebranopadol therapy according to an administration regimen wherein the administered daily dose of Cebranopadol is incrementally increased (titrated) minimizes adverse side effects associated with Cebranopadol, particularly dizziness, nausea and vomiting, while maintaining its therapeutic effectiveness which results in a greater tolerability of the drug during therapy. Preferably, the first daily dose of Cebranopadol is below 200 µg, e.g. about 100 µg, whereas the first administration interval lasts for at least 3 days, for at least 4 days, for at least 5 days, for at least 6 days, or for at least 7 days. Preferably, the second daily dose of Cebranopadol is about 200 µg or more, whereas the second administration interval lasts for another at least 3 days, for another at least 4 days, for another at least 5 days, for another at least 6 days, or for another at least 7 days.

It has been surprisingly found that particularly adverse events that are associated with the central nervous system, such as dizziness, can be minimized by titration according to the invention. As far as adverse events associated with the gastrointestinal tract are concerned, titration of Cebranopadol according the present invention is also advantageous, particularly with respect to nausea and vomiting.

Thus, discontinuations of treatment due to inacceptable treatment emergent adverse events can be minimized.

BRIEF DESCRIPTION OF THE DRAWINGS

FIG. 1 shows the dependency of the placebo corrected Cebranopadol effect as function of concentration, as provided by pharmacokinetic-pharmacodynamic modeling of clinical data from a dose-finding trial regarding low back pain.

FIGS. 2 and 3 show the probability of adverse events nausea, vomiting or dizziness as a function of days. FIG. 2 shows the probability of adverse events nausea, vomiting and dizziness as observed in a clinical trial where treatment was initiated with a daily dose of 200 µg which was later increased to a daily dose of 400 µg (■). These observed adverse events are compared with the simulated probabilities for two different titration regimes also reaching a final dose of 400 µg of Cebranopadol. FIG. 3 shows the probability of adverse events nausea, vomiting and dizziness as observed in a clinical trial where treatment was initiated with a daily dose of 200 µg which was later increased to a daily dose of 400 µg and subsequently to a final daily dose of 600 µg (■). These observed adverse events are compared with the simulated probabilities for two different titration regimens also reaching a final dose of 600 µg of Cebranopadol.

FIGS. 4 and 5 show the total dropout by different doses. FIG. 4 shows the total dropouts for placebo (●), 200 µg of Cebranopadol (■) or 400 µg of Cebranopadol (♦) in each case administered once daily without titration. These total dropouts are compared with the simulated results for two different titration regimes reaching a final dose of 400 µg of Cebranopadol. FIG. 5 shows the total dropouts for placebo (●), 200 µg of Cebranopadol (■), 400 µg of Cebranopadol (♦), or 600 µg of Cebranopadol (▲) in each case administered once daily without titration. These total dropouts are compared with the simulated results for three different titration regimens reaching a final dose of 600 µg of Cebranopadol.

FIG. 6 shows the probability of adverse events nausea, vomiting or dizziness as a function of days. The simulated results for different administration regimens each reaching a final daily dose of 600 µg of Cebranopadol are compared with one another.

FIG. 7 shows the total dropout by different doses. The simulated results for different administration regimens each reaching a final daily dose of 600 µg of Cebranopadol are compared with one another.

DETAILED DESCRIPTION OF THE INVENTION

Figure 1:
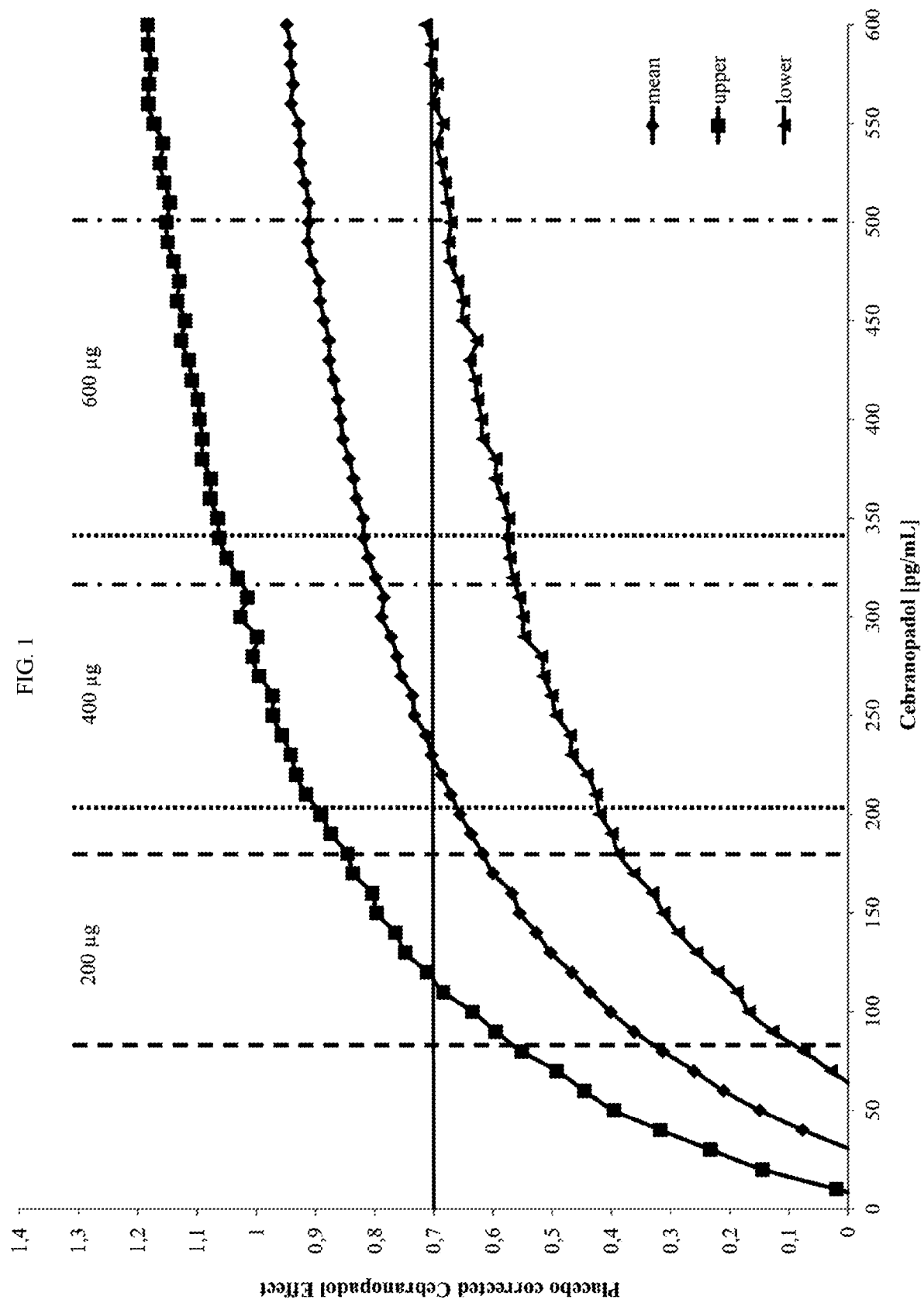
FIGS. 1 to 7 show results from pharmacometric analyses which were performed on clinical data from different trials.

For the purpose of the specification "titration" means that after a certain administration interval, the dose of Cebranopadol is altered, typically increased (or decreased) until the optimal dose is reached.

For the purpose of the specification, "treatment of pain" refers to any amelioration of pain, alleviation of pain or pain relief including the prevention thereof.

As used hereinafter, the term "Cebranopadol" is intended to include trans-6'-fluoro-4',9'-dihydro-N,N-dimethyl-4-phenyl-spiro[cyclohexane-1,1'-(3'H)-pyrano[3,4-b]indol]-4-amine (also referred to as (1r,4r)-6'-fluoro-N,N-dimethyl-4-phenyl-4',9'-dihydro-3'H-spiro[cyclohexane-1,1'-pyrano[3,4-b]indol]-4-amine), its pharmaceutically acceptable salts and solvates thereof:

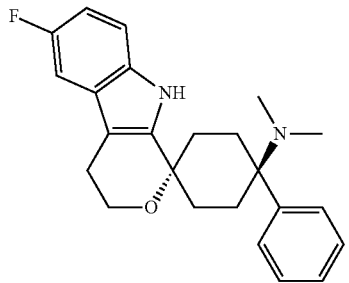 [SMILES: CN(C)[C@]1(c2ccccc2)CC[C@]2(CC1)OCCc1c3cc(F)ccc3[nH]c12]

Suitable pharmaceutically acceptable salts of Cebranopadol include salts of inorganic acids, such as hydrochloric acid (Cebranopadol HCl), hydrobromic acid and sulfuric acid, and salts of organic acids, such as methane sulfonic acid, fumaric acid, maleic acid, acetic acid, oxalic acid, succinic acid, malic acid, tartaric acid, mandelic acid, lactic acid, citric acid, glutamic acid, acetylsalicylic acid, nicotinic acid, aminobenzoic acid, α-liponic acid, hippuric acid and asparaginic acid. Preferably, Cebranopadol is present in the non-salt form (free base).

For the purpose of the specification, doses of Cebranopadol relate to the free base. Thus, when a pharmaceutically acceptable salt is used instead, its dose has to be adapted to the equivalent dose of the free base. For example, a dose of "200 μg" means an amount of 200 μg of the free base or any equivalent amount of a pharmaceutically acceptable salt or solvate corresponding to 200 μg of the free base.

Cebranopadol is administered according to an administration regimen comprising
(i) a first administration interval, which lasts for at least 1 day, preferably for at least 2 consecutive days, wherein a first daily dose of Cebranopadol is administered on every day of the first administration interval.

In a preferred embodiment, the first administration interval, independent of any subsequent administration interval, lasts for at least 3 consecutive days; more preferably at least 4 consecutive days; still more preferably at least 5 consecutive days; even more preferably from 3 to 14 consecutive days, preferably from 3 to 10 consecutive days, more preferably from 3 to 7 consecutive days; most preferably from 5 to 11 consecutive days, and in particular from 5 to 7 consecutive days. In another preferred embodiment, the first administration interval, independent of any subsequent administration interval, lasts for 2 to 6 consecutive days; more preferably 2 to 5 consecutive days; still more preferably 2 to 4 consecutive days; even more preferably 3 consecutive days.

In a preferred embodiment, the first daily dose of Cebranopadol is within the range of from 10 to 190 μg, more preferably 20 to 180 μg, still more preferably 30 to 170 μg, yet more preferably 40 to 160 μg, even more preferably 50 to 150 μg, most preferably 60 to 140 μg, and in particular 70 to 130 μg. In another preferred embodiment, the first daily dose of Cebranopadol is within the range of from 10 to 90 μg, more preferably 15 to 85 μg, still more preferably 20 to 80 μg, yet more preferably 25 to 75 μg, even more preferably 30 to 70 μg, most preferably 35 to 65 μg, and in particular 40 to 60 μg. Preferred first daily doses of Cebranopadol include but are not limited to about 25 μg, about 50 μg, about 75 μg, about 100 μg, and about 125 μg.

Preferably, the first daily dose of Cebranopadol can be regarded as being "subtherapeutic", i.e. below the therapeutically effective pain treating dose of Cebranopadol such that within a significant number of patients at the first day and the second day of the first administration interval does not provide statistically significant pain relief compared to placebo.

Said therapeutically effective pain treating dose of Cebranopadol may vary depending upon the pain to be treated. Based upon clinical data, a daily dose of 100 μg Cebranopadol can be regarded as being "subtherapeutic" with regard to the treatment of e.g. low back pain (see FIG. 1).

Preferably, on any day of the first administration interval, Cebranopadol is administered at the same administration frequency, which may be once daily (sid) or twice daily (bid), whereas administration once daily (sid) is particularly preferred.

When the first daily dose of Cebranopadol is administered twice daily, said first daily dose is preferably divided into two portions of approximately or exactly the same size, wherein one portion is administered during the day, e.g. in the morning, and the other portion is administered during the same day but after several hours, preferably after about 12 hours, e.g. in the evening.

The first daily dose of Cebranopadol may be administered orally, buccally, sublingually, transmucosally, intralumbally, intraperitoneally, transdermally, intravenously, intramuscularly, intragluteally, intracutaneously or subcutaneously, orally being most preferred.

According to a preferred embodiment,
the first daily dose of Cebranopadol is less than 200 μg; and/or
the first administration interval lasts for at least 4 consecutive days.

Cebranopadol is administered according to an administration regimen comprising
(ii) a second administration interval, which lasts for at least 1 day, preferably for at least 2 consecutive days and directly follows the first administration interval without interruption, wherein a second daily dose of Cebranopadol is administered on every day of the second administration interval.

The second administration interval directly follows the first administration interval without interruption. Thus, for example, when the first administration interval comprises 2 days and commences on Monday, the first administration interval lasts until Tuesday of the same week, whereas the second administration interval commences on Wednesday of the same week.

In a preferred embodiment, the second administration interval, independent of any preceding or subsequent administration intervals, lasts for at least 3 consecutive days; more preferably at least 4 consecutive days; still more preferably at least 5 consecutive days; even more preferably from 3 to 14 consecutive days, preferably from 3 to 10 consecutive days, more preferably from 3 to 7 consecutive days; most preferably from 5 to 11 consecutive days; and in particular from 5 to 7 consecutive days. In another preferred embodiment, the second administration interval, independent of any subsequent administration interval, lasts for 2 to 6 consecutive days; more preferably 2 to 5 consecutive days; still more preferably 2 to 4 consecutive days; even more preferably 3 consecutive days.

In a preferred embodiment, the second daily dose of Cebranopadol is within the range of from 110 to 290 µg, more preferably 120 to 280 µg, still more preferably 130 to 270 µg, yet more preferably 140 to 260 µg, even more preferably 150 to 250 µg, most preferably 160 to 240 µg, and in particular 170 to 230 µg. In another preferred embodiment, the second daily dose of Cebranopadol is within the range of from 10 to 190 µg, more preferably 20 to 180 µg, still more preferably 30 to 170 µg, yet more preferably 40 to 160 µg, even more preferably 50 to 150 µg, most preferably 60 to 140 µg, and in particular 70 to 130 µg. Preferred second daily doses of Cebranopadol include but are not limited to about 75 µg, about 100 µg, about 125 µg, about 150 µg, about 175 µg, about 200 µg, about 225 µg, and about 250 µg.

administration interval, Cebranopadol is administered once daily (sid) at a constant second daily dose for a second administration interval, with the proviso that the second daily dose of Cebranopadol is higher than the first daily dose Cebranopadol.

Preferably, the first daily dose of Cebranopadol is within the range of from 10 to 90 wt-% of the second daily dose of Cebranopadol, more preferably from 20 to 80 wt.-%, still more preferably from 30 to 70 wt.-%, most preferably from 40 to 60 wt.-%.

In preferred embodiments, the ratio of first daily dose of Cebranopadol: second daily dose of Cebranopadol ([µg] ±5%:[µg]±5%) is selected from the group consisting of

| | | | | | | | | |
|---|---|---|---|---|---|---|---|---|
| 25:50 | 25:75 | 25:100 | 25:125 | 25:150 | 25:175 | 25:200 | 25:225 | 25:250 |
| 25:275 | 25:300 | 50:75 | 50:100 | 50:125 | 50:150 | 50:175 | 50:200 | 50:225 |
| 50:250 | 50:275 | 50:300 | 75:100 | 75:125 | 75:150 | 75:175 | 75:200 | 75:225 |
| 75:250 | 75:275 | 75:300 | 100:125 | 100:150 | 100:175 | 100:200 | 100:225 | 100:250 |
| 100:275 | 100:300 | 125:150 | 125:175 | 125:200 | 125:225 | 125:250 | 125:275 | 125:300 |
| 150:175 | 150:200 | 150:225 | 150:250 | 150:275 | 150:300 | 175:200 | 175:225 | 175:250 |
| 175:275 | 175:300 | 200:225 | 200:250 | 200:275 | 200:300 | 225:250 | 225:275 | 225:300 |
| 250:275 | 250:300 | 275:300 | | | | | | |

Preferably, on any day of the second administration interval, Cebranopadol is administered at the same administration frequency, which may be once daily (sid) or twice daily (bid), whereas administration once daily (sid) is particularly preferred.

When the second daily dose of Cebranopadol is administered twice daily, said second daily dose is preferably divided into two portions of approximately or exactly the same size, wherein one portion is administered during the day, e.g. in the morning, and the other portion is administered during the same day but after several hours, preferably after about 12 hours, e.g. in the evening.

The second daily dose of Cebranopadol may be administered orally, buccally, sublingually, transmucosally, intralumbally, intraperitoneally, transdermally, intravenously, intramuscularly, intragluteally, intracutaneously or subcutaneously, orally being most preferred.

The first daily dose of Cebranopadol is lower than the second daily dose of Cebranopadol.

In a preferred embodiment, the administration regimen is dynamic, i.e. the dose is successively increased until the optimal, pharmaceutically effective dose for the individual subject has been reached. The optimal dose may vary individually and also depends upon the type and degree of pain to be treated. Preferably, the optimal dose is defined as the dose providing a meaningful improvement of pain with acceptable side effects in the patient's perception (maximum therapeutic benefit). The regimen results in a lower incidence or severity of side effects, such as dizziness, nausea and vomiting.

Preferably, the subject monitors the achievement of amelioration of pain and the occurrence of side effects caused by the current dose of Cebranopadol. Depending upon the assessment of the desired pain reduction on the one hand and the adverse events on the other hand, the subject decides whether the dose of Cebranopadol is further increased (next titration step upwards),
maintained at the current level (no further titration step) or
decreased (next titration step downwards).

Preferably, during the titration phase Cebranopadol is administered once daily (sid) at a constant first (initial) daily dose for a first administration interval. After said first wherein preferably according to each of the above preferred embodiments, preferably the first administration interval as well as the second administration interval each last for at least 3 consecutive days; more preferably at least 4 consecutive days; still more preferably at least 5 consecutive days; even more preferably from 3 to 14 consecutive days, preferably from 3 to 10 consecutive days, more preferably from 3 to 7 consecutive days; most preferably from 5 to 11 consecutive days; and in particular from 5 to 7 consecutive days.

For example, a ratio of first daily dose:second daily dose of 100:200 means that the first daily dose of Cebranopadol that is administered on every day of the first administration interval amounts to 100 µg±5%, i.e. to a range of from 95 µg to 105 µg, whereas the second daily dose of Cebranopadol that is administered on every day of the second administration interval amounts to 200 µg±5%, i.e. to a range of from 190 µg to 210 µg.

After said second administration interval, the titration phase may be terminated, i.e. administration of Cebranopadol may be continued at the second daily dose of Cebranopadol, thereby initiating the continuous phase. Under these circumstances, the titration phase is terminated by the fact that the dose of Cebranopadol that was administered during the second administration interval is not further increased (or decreased).

Accordingly, in a preferred embodiment, the administration regimen is biphasic (2 consecutive administration intervals). Preferably, said biphasic administration regimen comprises at least 2, at least 3, at least 4, at least 5, at least 6, at least 7, at least 8, at least 9, at least 10, at least 11, at least 12, at least 13, or at least 14 days; the first daily dose of Cebranopadol during the first administration interval is within the range of from 50 µg±5% to 150 µg±5%, preferably administered orally once daily (sid); and the second daily dose of Cebranopadol during the second administration interval is within the range of from 150 µg±5%, to 250 µg±5%, preferably administered orally once daily (sid). Preferably, the second administration interval commences 3 to 9 days, or 3 to 7 days, more preferably 4 to 8 days, still more preferably 5 to 7 days after initiation of administration of Cebranopadol with the first administration interval.

Alternatively, after said second administration interval, the titration phase may continue, i.e. Cebranopadol is administered at a third daily dose for a third administration interval, with the proviso that the third dose is higher than the second dose.

Therefore, in a preferred embodiment, Cebranopadol is administered according to an administration regimen additionally comprising
(iii) a third administration interval, which lasts for at least 1 day, preferably for at least 2 consecutive days and directly follows the second administration interval without interruption, wherein a third daily dose of Cebranopadol is administered on every day of the third administration interval;
wherein the second daily dose of Cebranopadol is lower than the third daily dose of Cebranopadol.

The third administration interval directly follows the second administration interval without interruption.

In a preferred embodiment, the third administration interval, independent of any preceding or subsequent administration intervals, lasts for at least 3 consecutive days; more preferably at least 4 consecutive days; still more preferably at least 5 consecutive days; even more preferably from 3 to 14 consecutive days, preferably from 3 to 10 consecutive days, more preferably from 3 to 7 consecutive days; most preferably from 5 to 11 consecutive days; and in particular from 5 to 7 consecutive days. In another preferred embodiment, the third administration interval, independent of any subsequent administration interval, lasts for 2 to 6 consecutive days; more preferably 2 to 5 consecutive days; still more preferably 2 to 4 consecutive days; even more preferably 3 consecutive days.

In a preferred embodiment, the third daily dose of Cebranopadol is within the range of from 310 to 490 µg, more preferably 320 to 480 µg, still more preferably 330 to 470 µg, yet more preferably 340 to 460 µg, even more preferably 350 to 450 µg, most preferably 360 to 440 µg, and in particular 370 to 430 µg. In another preferred embodiment, the third daily dose of Cebranopadol is within the range of from 110 to 290 µg, more preferably 120 to 280 µg, still more preferably 130 to 270 µg, yet more preferably 140 to 260 µg, even more preferably 150 to 250 µg, most preferably 160 to 240 µg, and in particular 170 to 230 µg. Preferred third daily doses of Cebranopadol include but are not limited to about 150 µg, about 175 µg, about 200 µg, about 225 µg, about 250 µg, about 275 µg, about 300 µg, about 325 µg, about 350 µg, about 375 µg, about 400 µg, about 425 µg, and about 450 µg.

Preferably, on any day of the third administration interval, Cebranopadol is to administered at the same administration frequency, which may be once daily (sid) or twice daily (bid), whereas administration once daily (sid) is particularly preferred.

When the third daily dose of Cebranopadol is administered twice daily, said third daily dose is preferably divided into two portions of approximately or exactly the same size, wherein one portion is administered during the day, e.g. in the morning, and the other portion is administered during the same day but after several hours, preferably after about 12 hours, e.g. in the evening.

The third daily dose of Cebranopadol may be administered orally, buccally, sublingually, transmucosally, intralumbally, intraperitoneally, transdermally, intravenously, intramusculously, intragluteally, intracutaneously or subcutaneously, orally being most preferred.

When Cebranopadol is administered according to an administration regimen additionally comprising a third administration interval, the second daily dose of Cebranopadol is lower than the third daily dose of Cebranopadol.

Preferably,
the first daily dose of Cebranopadol is within the range of from 5 to 45 wt.-% of the third daily dose of Cebranopadol, more preferably from 10 to 40 wt.-%, still more preferably from 15 to 35 wt.-%, most preferably from 20 to 30 wt.-%; and/or
the second daily dose of Cebranopadol is within the range of from 30 to 70 wt.-% of the third daily dose of Cebranopadol, more preferably from 35 to 65 wt.-%, still more preferably from 40 to 60 wt.-%, most preferably from 45 to 55 wt.-%.

In preferred embodiments, the ratio of first daily dose of Cebranopadol:second daily dose of Cebranopadol:third daily dose of Cebranopadol ([µg]±5%:[µg]±5%:[µg]±5%) is selected from the group consisting of

| | | | | | |
|---|---|---|---|---|---|
| 25:50:75 | 25:50:100 | 25:50:125 | 25:50:150 | 25:50:175 | 25:50:200 |
| 25:50:225 | 25:50:250 | 25:50:275 | 25:50:300 | 25:50:325 | 25:50:350 |
| 25:50:375 | 25:50:400 | 25:50:425 | 25:50:450 | 25:50:475 | 25:50:500 |
| 25:75:100 | 25:75:125 | 25:75:150 | 25:75:175 | 25:75:200 | 25:75:225 |
| 25:75:250 | 25:75:275 | 25:75:300 | 25:75:325 | 25:75:350 | 25:75:375 |
| 25:75:400 | 25:75:425 | 25:75:450 | 25:75:475 | 25:75:500 | 25:100:125 |
| 25:100:150 | 25:100:175 | 25:100:200 | 25:100:225 | 25:100:250 | 25:100:275 |
| 25:100:300 | 25:100:325 | 25:100:350 | 25:100:375 | 25:100:400 | 25:100:425 |
| 25:100:450 | 25:100:475 | 25:100:500 | 25:125:150 | 25:125:175 | 25:125:200 |
| 25:125:225 | 25:125:250 | 25:125:275 | 25:125:300 | 25:125:325 | 25:125:350 |
| 25:125:375 | 25:125:400 | 25:125:425 | 25:125:450 | 25:125:475 | 25:125:500 |
| 25:150:175 | 25:150:200 | 25:150:225 | 25:150:250 | 25:150:275 | 25:150:300 |
| 25:150:325 | 25:150:350 | 25:150:375 | 25:150:400 | 25:150:425 | 25:150:450 |
| 25:150:475 | 25:150:500 | 25:175:200 | 25:175:225 | 25:175:250 | 25:175:275 |
| 25:175:300 | 25:175:325 | 25:175:350 | 25:175:375 | 25:175:400 | 25:175:425 |
| 25:175:450 | 25:175:475 | 25:175:500 | 25:200:225 | 25:200:250 | 25:200:275 |
| 25:200:300 | 25:200:325 | 25:200:350 | 25:200:375 | 25:200:400 | 25:200:425 |
| 25:200:450 | 25:200:475 | 25:200:500 | 25:225:250 | 25:225:275 | 25:225:300 |
| 25:225:325 | 25:225:350 | 25:225:375 | 25:225:400 | 25:225:425 | 25:225:450 |
| 25:225:475 | 25:225:500 | 25:250:275 | 25:250:300 | 25:250:325 | 25:250:350 |
| 25:250:375 | 25:250:400 | 25:250:425 | 25:250:450 | 25:250:475 | 25:250:500 |
| 25:275:300 | 25:275:325 | 25:275:350 | 25:275:375 | 25:275:400 | 25:275:425 |
| 25:275:450 | 25:275:475 | 25:275:500 | 25:300:325 | 25:300:350 | 25:300:375 |
| 25:300:400 | 25:300:425 | 25:300:450 | 25:300:475 | 25:300:500 | |

| | | | | | |
|---|---|---|---|---|---|
| 50:75:100 | 50:75:125 | 50:75:150 | 50:75:175 | 50:75:200 | 50:75:225 |
| 50:75:250 | 50:75:275 | 50:75:300 | 50:75:325 | 50:75:350 | 50:75:375 |
| 50:75:400 | 50:75:425 | 50:75:450 | 50:75:475 | 50:75:500 | 50:100:125 |
| 50:100:150 | 50:100:175 | 50:100:200 | 50:100:225 | 50:100:250 | 50:100:275 |
| 50:100:300 | 50:100:325 | 50:100:350 | 50:100:375 | 50:100:400 | 50:100:425 |
| 50:100:450 | 50:100:475 | 50:100:500 | 50:125:150 | 50:125:175 | 50:125:200 |
| 50:125:225 | 50:125:250 | 50:125:275 | 50:125:300 | 50:125:325 | 50:125:350 |
| 50:125:375 | 50:125:400 | 50:125:425 | 50:125:450 | 50:125:475 | 50:125:500 |
| 50:150:175 | 50:150:200 | 50:150:225 | 50:150:250 | 50:150:275 | 50:150:300 |
| 50:150:325 | 50:150:350 | 50:150:375 | 50:150:400 | 50:150:425 | 50:150:450 |
| 50:150:475 | 50:150:500 | 50:175:200 | 50:175:225 | 50:175:250 | 50:175:275 |
| 50:175:300 | 50:175:325 | 50:175:350 | 50:175:375 | 50:175:400 | 50:175:425 |
| 50:175:450 | 50:175:475 | 50:175:500 | 50:200:225 | 50:200:250 | 50:200:275 |
| 50:200:300 | 50:200:325 | 50:200:350 | 50:200:375 | 50:200:400 | 50:200:425 |
| 50:200:450 | 50:200:475 | 50:200:500 | 50:225:250 | 50:225:275 | 50:225:300 |
| 50:225:325 | 50:225:350 | 50:225:375 | 50:225:400 | 50:225:425 | 50:225:450 |
| 50:225:475 | 50:225:500 | 50:250:275 | 50:250:300 | 50:250:325 | 50:250:350 |
| 50:250:375 | 50:250:400 | 50:250:425 | 50:250:450 | 50:250:475 | 50:250:500 |
| 50:275:300 | 50:275:325 | 50:275:350 | 50:275:375 | 50:275:400 | 50:275:425 |
| 50:275:450 | 50:275:475 | 50:275:500 | 50:300:325 | 50:300:350 | 50:300:375 |
| 50:300:400 | 50:300:425 | 50:300:450 | 50:300:475 | 50:300:500 | |

| | | | | | |
|---|---|---|---|---|---|
| 75:100:125 | 75:100:150 | 75:100:175 | 75:100:200 | 75:100:225 | 75:100:250 |
| 75:100:275 | 75:100:300 | 75:100:325 | 75:100:350 | 75:100:375 | 75:100:400 |
| 75:100:425 | 75:100:450 | 75:100:475 | 75:100:500 | 75:125:150 | 75:125:175 |
| 75:125:200 | 75:125:225 | 75:125:250 | 75:125:275 | 75:125:300 | 75:125:325 |
| 75:125:350 | 75:125:375 | 75:125:400 | 75:125:425 | 75:125:450 | 75:125:475 |

| | | | | | |
|---|---|---|---|---|---|
| 75:125:500 | 75:150:175 | 75:150:200 | 75:150:225 | 75:150:250 | 75:150:275 |
| 75:150:300 | 75:150:325 | 75:150:350 | 75:150:375 | 75:150:400 | 75:150:425 |
| 75:150:450 | 75:150:475 | 75:150:500 | 75:175:200 | 75:175:225 | 75:175:250 |
| 75:175:275 | 75:175:300 | 75:175:325 | 75:175:350 | 75:175:375 | 75:175:400 |
| 75:175:425 | 75:175:450 | 75:175:475 | 75:175:500 | 75:200:225 | 75:200:250 |
| 75:200:275 | 75:200:300 | 75:200:325 | 75:200:350 | 75:200:375 | 75:200:400 |
| 75:200:425 | 75:200:450 | 75:200:475 | 75:200:500 | 75:225:250 | 75:225:275 |
| 75:225:300 | 75:225:325 | 75:225:350 | 75:225:375 | 75:225:400 | 75:225:425 |
| 75:225:450 | 75:225:475 | 75:225:500 | 75:250:275 | 75:250:300 | 75:250:325 |
| 75:250:350 | 75:250:375 | 75:250:400 | 75:250:425 | 75:250:450 | 75:250:475 |
| 75:250:500 | 75:275:300 | 75:275:325 | 75:275:350 | 75:275:375 | 75:275:400 |
| 75:275:425 | 75:275:450 | 75:275:475 | 75:275:500 | 75:300:325 | 75:300:350 |
| 75:300:375 | 75:300:400 | 75:300:425 | 75:300:450 | 75:300:475 | 75:300:500 |

| | | | | | |
|---|---|---|---|---|---|
| 100:125:150 | 100:125:175 | 100:125:200 | 100:125:225 | 100:125:250 | 100:125:275 |
| 100:125:300 | 100:125:325 | 100:125:350 | 100:125:375 | 100:125:400 | 100:125:425 |
| 100:125:450 | 100:125:475 | 100:125:500 | 100:150:175 | 100:150:200 | 100:150:225 |
| 100:150:250 | 100:150:275 | 100:150:300 | 100:150:325 | 100:150:350 | 100:150:375 |
| 100:150:400 | 100:150:425 | 100:150:450 | 100:150:475 | 100:150:500 | 100:175:200 |
| 100:175:225 | 100:175:250 | 100:175:275 | 100:175:300 | 100:175:325 | 100:175:350 |
| 100:175:375 | 100:175:400 | 100:175:425 | 100:175:450 | 100:175:475 | 100:175:500 |
| 100:200:225 | 100:200:250 | 100:200:275 | 100:200:300 | 100:200:325 | 100:200:350 |
| 100:200:375 | 100:200:400 | 100:200:425 | 100:200:450 | 100:200:475 | 100:200:500 |
| 100:225:250 | 100:225:275 | 100:225:300 | 100:225:325 | 100:225:350 | 100:225:375 |
| 100:225:400 | 100:225:425 | 100:225:450 | 100:225:475 | 100:225:500 | 100:250:275 |
| 100:250:300 | 100:250:325 | 100:250:350 | 100:250:375 | 100:250:400 | 100:250:425 |
| 100:250:450 | 100:250:475 | 100:250:500 | 100:275:300 | 100:275:325 | 100:275:350 |
| 100:275:375 | 100:275:400 | 100:275:425 | 100:275:450 | 100:275:475 | 100:275:500 |
| 100:300:325 | 100:300:350 | 100:300:375 | 100:300:400 | 100:300:425 | 100:300:450 |
| 100:300:475 | 100:300:500 | | | | |

| | | | | | |
|---|---|---|---|---|---|
| 125:150:175 | 125:150:200 | 125:150:225 | 125:150:250 | 125:150:275 | 125:150:300 |
| 125:150:325 | 125:150:350 | 125:150:375 | 125:150:400 | 125:150:425 | 125:150:450 |
| 125:150:475 | 125:150:500 | 125:175:200 | 125:175:225 | 125:175:250 | 125:175:275 |
| 125:175:300 | 125:175:325 | 125:175:350 | 125:175:375 | 125:175:400 | 125:175:425 |
| 125:175:450 | 125:175:475 | 125:175:500 | 125:200:225 | 125:200:250 | 125:200:275 |
| 125:200:300 | 125:200:325 | 125:200:350 | 125:200:375 | 125:200:400 | 125:200:425 |
| 125:200:450 | 125:200:475 | 125:200:500 | 125:225:250 | 125:225:275 | 125:225:300 |
| 125:225:325 | 125:225:350 | 125:225:375 | 125:225:400 | 125:225:425 | 125:225:450 |
| 125:225:475 | 125:225:500 | 125:250:275 | 125:250:300 | 125:250:325 | 125:250:350 |
| 125:250:375 | 125:250:400 | 125:250:425 | 125:250:450 | 125:250:475 | 125:250:500 |
| 125:275:300 | 125:275:325 | 125:275:350 | 125:275:375 | 125:275:400 | 125:275:425 |
| 125:275:450 | 125:275:475 | 125:275:500 | 125:300:325 | 125:300:350 | 125:300:375 |
| 125:300:400 | 125:300:425 | 125:300:450 | 125:300:475 | 125:300:500 | |

| | | | | | |
|---|---|---|---|---|---|
| 150:175:200 | 150:175:225 | 150:175:250 | 150:175:275 | 150:175:300 | 150:175:325 |
| 150:175:350 | 150:175:375 | 150:175:400 | 150:175:425 | 150:175:450 | 150:175:475 |
| 150:175:500 | 150:200:225 | 150:200:250 | 150:200:275 | 150:200:300 | 150:200:325 |
| 150:200:350 | 150:200:375 | 150:200:400 | 150:200:425 | 150:200:450 | 150:200:475 |
| 150:200:500 | 150:225:250 | 150:225:275 | 150:225:300 | 150:225:325 | 150:225:350 |
| 150:225:375 | 150:225:400 | 150:225:425 | 150:225:450 | 150:225:475 | 150:225:500 |
| 150:250:275 | 150:250:300 | 150:250:325 | 150:250:350 | 150:250:375 | 150:250:400 |
| 150:250:425 | 150:250:450 | 150:250:475 | 150:250:500 | 150:275:300 | 150:275:325 |
| 150:275:350 | 150:275:375 | 150:275:400 | 150:275:425 | 150:275:450 | 150:275:475 |
| 150:275:500 | 150:300:325 | 150:300:350 | 150:300:375 | 150:300:400 | 150:300:425 |
| 150:300:450 | 150:300:475 | 150:300:500 | | | |

| | | | | | |
|---|---|---|---|---|---|
| 175:200:225 | 175:200:250 | 175:200:275 | 175:200:300 | 175:200:325 | 175:200:350 |
| 175:200:375 | 175:200:400 | 175:200:425 | 175:200:450 | 175:200:475 | 175:200:500 |
| 175:225:250 | 175:225:275 | 175:225:300 | 175:225:325 | 175:225:350 | 175:225:375 |
| 175:225:400 | 175:225:425 | 175:225:450 | 175:225:475 | 175:225:500 | 175:250:275 |
| 175:250:300 | 175:250:325 | 175:250:350 | 175:250:375 | 175:250:400 | 175:250:425 |
| 175:250:450 | 175:250:475 | 175:250:500 | 175:275:300 | 175:275:325 | 175:275:350 |
| 175:275:375 | 175:275:400 | 175:275:425 | 175:275:450 | 175:275:475 | 175:275:500 |
| 175:300:325 | 175:300:350 | 175:300:375 | 175:300:400 | 175:300:425 | 175:300:450 |
| 175:300:475 | 175:300:500 | | | | | wherein preferably according to each of the above preferred embodiments, preferably the first administration interval as well as the second administration interval as well as the third administration interval each last for at least 3 consecutive days; more preferably at least 4 consecutive days; still more preferably at least 5 consecutive days; even more preferably from 3 to 14 consecutive days, preferably from 3 to 10 consecutive days, more preferably from 3 to 7 consecutive days; most preferably from 5 to 11 consecutive days; and in particular from 5 to 7 consecutive days.

After said third administration interval, the titration phase may be terminated, i.e. administration of Cebranopadol may be continued at the third daily dose, thereby initiating the continuous phase.

Accordingly, in a preferred embodiment, the administration regimen is triphasic (3 consecutive administration intervals). Preferably, said triphasic administration regimen comprises at least 3, at least 4, at least 5, at least 6, at least 7, at least 8, at least 9, at least 10, at least 11, at least 12, at least 13, at least 14 days, at least 15 days, at least 16 days, at least 17 days, at least 18 days, at least 19 days, at least 20 days, or at least 21 days; the first daily dose of Cebranopadol during the first administration interval is within the range of from 50 µg±5% to 150 µg±5%, preferably administered orally once daily (sid); the second daily dose of Cebranopadol during the second administration interval is within the range of from 150 µg±5% to 250 µg±5%, preferably administered orally once daily (sid); and the third daily dose of Cebranopadol during the third administration interval is within the range of from 350 µg±5% to 450 µg±5%, preferably administered orally once daily (sid). Preferably, the second administration interval commences 3 to 9 days, more preferably 4 to 8 days, still more preferably 5 to 7 days after initiation of administration of Cebranopadol with the first administration interval, and the third administration interval commences 3 to 9 days, more preferably 4 to 8 days, still more preferably 5 to 7 days after initiation of the second administration interval.

Alternatively, after said third administration interval, the titration phase may continue, i.e. Cebranopadol is administered at a fourth daily dose for a fourth administration interval. At this stage the fourth daily dose of Cebranopadol may be either further increased or decreased, depending on the individual needs of the subject.

Therefore, in a preferred embodiment, Cebranopadol is administered according to an administration regimen comprising the preferred third administration interval described above and additionally comprising (iv) a fourth administration interval, which lasts for at least 1 day, preferably for at least 2 consecutive days and directly follows the third administration interval without interruption, wherein a fourth daily dose of Cebranopadol is administered on every day of the fourth administration interval;

wherein the third daily dose of Cebranopadol is lower than the fourth daily dose of Cebranopadol.

When Cebranopadol is administered according to an administration regimen additionally comprising a fourth administration interval, the fourth administration interval directly follows the third administration interval without interruption.

In a preferred embodiment, the fourth administration interval, independent of any preceding or subsequent administration intervals, lasts for at least 3 consecutive days; more preferably at least 4 consecutive days; still more preferably at least 5 consecutive days; even more preferably from 3 to 14 consecutive days, preferably from 3 to 10 consecutive days, more preferably from 3 to 7 consecutive days; most preferably from 5 to 11 consecutive days; and in particular from 5 to 7 consecutive days. In another preferred embodiment, the fourth administration interval, independent of any subsequent administration interval, lasts for 2 to 6 consecutive days; more preferably 2 to 5 consecutive days; still more preferably 2 to 4 consecutive days; even more preferably 3 consecutive days.

In a preferred embodiment, the fourth daily dose of Cebranopadol is within the range of from 510 to 690 µg, more preferably 520 to 680 µg, still more preferably 530 to 670 µg, yet more preferably 540 to 660 µg, even more preferably 550 to 650 µg, most preferably 560 to 640 µg, and in particular 570 to 630 µg. In another preferred embodiment, the fourth daily dose of Cebranopadol is within the range of from 210 to 390 µg, more preferably 220 to 380 µg, still more preferably 230 to 370 µg, yet more preferably 240 to 360 µg, even more preferably 250 to 350 µg, most preferably 260 to 340 µg, and in particular 270 to 330 µg. Preferred fourth daily doses of Cebranopadol include but are not limited to about 250 µg, about 275 µg, about 300 µg, about 325 µg, about 350 µg, about 375 µg, about 400 µg, about 425 µg, about 450 µg, about 475 µg, about 500 µg, about 525 µg, about 550 µg, about 575 µg, about 600 µg, about 625 µg, and about 650 µg.

Preferably, on any day of the fourth administration interval, Cebranopadol is administered at the same administration frequency, which may be once daily (sid) or twice daily (bid), whereas administration once daily (sid) is particularly preferred.

When the fourth daily dose of Cebranopadol is administered twice daily, said fourth daily dose is preferably divided into two portions of approximately or exactly the same size, wherein one portion is administered during the day, e.g. in the morning, and the other portion is administered during the same day but after several hours, preferably after about 12 hours, e.g. in the evening.

The fourth daily dose of Cebranopadol may be administered orally, buccally, sublingually, transmucosally, intralumbally, intraperitoneally, transdermally, intravenously, intramusculously, intragluteally, intracutaneously or subcutaneously, orally being most preferred.

The third daily dose of Cebranopadol is lower than the fourth daily dose of Cebranopadol.

Preferably, the first daily dose of Cebranopadol is within the range of from 5 to 30 wt.-% of the fourth daily dose of Cebranopadol, more preferably from 10 to 25 wt.-%, still more preferably from 15 to 20 wt.-%; and/or the second daily dose of Cebranopadol is within the range of from 15 to 50 wt.-% of the fourth daily dose of Cebranopadol, more preferably from 20 to 45 wt.-%, still more preferably from 25 to 40 wt.-%, most preferably from 30 to 35 wt.-%; and/or the third daily dose of Cebranopadol is within the range of from 50 to 75 wt.-% of the fourth daily dose of Cebranopadol, more preferably from 55 to 80 wt.-%, still more preferably from 60 to 75 wt.-%, most preferably from 65 to 70 wt.-%.

After said fourth administration interval, the titration phase may be terminated, i.e. administration of Cebranopadol may be continued at the fourth daily dose, thereby initiating the continuous phase.

Accordingly, in a preferred embodiment, the administration regimen is tetraphasic (4 consecutive administration intervals). Preferably, said tetraphasic administration regimen comprises at least 4, at least 5, at least 6, at least 7, at least 8, at least 9, at least 10, at least 11, at least 12, at least 13, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, or at least 28 days; the first daily dose of Cebranopadol during the first administration interval is within the range of from 50 µg±5% to 150 µg±5%, preferably administered orally once daily (sid); the second daily dose of Cebranopadol during the second administration interval is within the range of from 150 µg±5% to 250 µg±5%, preferably administered orally once daily (sid); the third daily dose of Cebranopadol during the third administration interval is within the range of from 350 µg±5% to 450 µg±5%, preferably administered orally once daily (sid); and the fourth daily dose of Cebranopadol during the fourth administration interval is within the range of from 550 µg±5% to 650 µg±5%, preferably administered orally once daily (sid). Preferably, the second administration interval commences 3 to 9 days, more preferably 4 to 8 days, still more preferably 5 to 7 days after initiation of administration of Cebranopadol with the first administration interval, the third administration interval commences 3 to 9 days, more preferably 4 to 8 days, still more preferably 5 to 7 days after initiation of the second administration interval, and the fourth administration interval commences 3 to 9 days, more preferably 4 to 8 days, still more preferably 5 to 7 days after initiation of the third administration interval.

Alternatively, after said fourth administration interval, the titration phase may continue, i.e. Cebranopadol is administered at a fifth daily dose for a fifth administration interval. At this stage the fifth daily dose of Cebranopadol may be either further increased or decreased, depending on the individual needs of the subject.

Therefore, in a preferred embodiment, Cebranopadol is administered according to an administration regimen comprising the preferred fourth administration interval described above and additionally comprising (iv) a fifth administration interval, which lasts for at least 1 day, preferably for at least 2 consecutive days and directly follows the fourth administration interval without interruption, wherein a fifth daily dose of Cebranopadol is administered on every day of the fifth administration interval;

wherein the fourth daily dose of Cebranopadol is lower than the fifth daily dose of Cebranopadol.

The fifth administration interval directly follows the fourth administration interval without interruption.

Preferably, the fifth administration interval, independent of any preceding or subsequent administration intervals, lasts for 2 to 6 consecutive days; more preferably 2 to 5 consecutive days; still more preferably 2 to 4 consecutive days; even more preferably 3 consecutive days.

Preferably, the fifth daily dose of Cebranopadol is within the range of from 310 to 490 µg, more preferably 320 to 480 µg, still more preferably 330 to 470 µg, yet more preferably 340 to 460 µg, even more preferably 350 to 450 µg, most preferably 360 to 440 µg, and in particular 370 to 430 µg. Preferred fifth daily doses of Cebranopadol include but are not limited to about 350 µg, about 375 µg, about 400 µg, about 425 µg, and about 450 µg.

Preferably, on any day of the fifth administration interval, Cebranopadol is administered at the same administration frequency, which may be once daily (sid) or twice daily (bid), whereas administration once daily (sid) is particularly preferred.

When the fifth daily dose of Cebranopadol is administered twice daily, said fifth daily dose is preferably divided into two portions of approximately or exactly the same size, wherein one portion is administered during the day, e.g. in the morning, and the other portion is administered during the same day but after several hours, preferably after about 12 hours, e.g. in the evening.

The fifth daily dose of Cebranopadol may be administered orally, buccally, sublingually, transmucosally, intralumbally, intraperitoneally, transdermally, intravenously, intramusculously, intragluteally, intracutaneously or subcutaneously, orally being most preferred.

When Cebranopadol is administered according to an administration regimen additionally comprising a fifth administration interval, the fourth daily dose of Cebranopadol is lower than the fifth daily dose of Cebranopadol.

Preferably,
the first daily dose of Cebranopadol is within the range of from 5.0 to 20 wt.-% of the fifth daily dose of Cebranopadol, more preferably from 7.5 to 17.5 wt.-%, still more preferably from 10 to 15 wt.-%; and/or the second daily dose of Cebranopadol is within the range of from 7.5 to 45 wt.-% of the fifth daily dose of Cebranopadol, more preferably from 10 to 40 wt.-%, still more preferably from 15 to 35 wt.-%, most preferably from 20 to 30 wt.-%; and/or the third daily dose of Cebranopadol is within the range of from 30 to 70 wt.-% of the fifth daily dose of Cebranopadol, more preferably from 35 to 65 wt.-%, still more preferably from 40 to 60 wt.-%, most preferably from 45 to 55 wt.-%; and/or the fourth daily dose of Cebranopadol is within the range of from 55 to 95 wt.-% of the fifth daily dose of Cebranopadol, more preferably from 60 to 90 wt.-%, still more preferably from 65 to 85 wt.-%, most preferably from 70 to 80 wt.-%.

After said fifth administration interval, the titration phase may be terminated, i.e. administration of Cebranopadol may be continued at the fifth daily dose, thereby initiating the continuous phase.

Accordingly, in a preferred embodiment, the administration regimen is pentaphasic (5 consecutive administration intervals). Preferably, said pentaphasic administration regimen comprises at least 4, at least 5, at least 6, at least 7, at least 8, at least 9, at least 10, at least 11, at least 12, at least 13, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, or at least 28 days; the first daily dose of Cebranopadol during the first administration interval is within the range of from 25 µg±5% to 75 µg±5%, preferably administered orally once daily (sid); the second daily dose of Cebranopadol during the second administration interval is within the range of from 50 µg±5% to 150 µg±5%, preferably administered orally once daily (sid); the third daily dose of Cebranopadol during the third administration interval is within the range of from 150 µg±5% to 250 µg±5%, preferably administered orally once daily (sid); the fourth daily dose of Cebranopadol during the fourth administration interval is within the range of from 250 µg±5% to 350 µg±5%, preferably administered orally once daily (sid); and the fifth daily dose of Cebranopadol during the fifth administration interval is within the range of from 350 µg±5% to 450 µg±5%, preferably administered orally once daily (sid). Preferably, the second administration interval commences 2 to 4 days, more preferably 3 days after initiation of administration of Cebranopadol with the first administration interval, the third administration interval commences 2 to 4 days, more preferably 3 days after initiation of the second administration interval, and the fourth administration interval commences 2 to 4 days, more preferably 3 days after initiation of the third administration interval, and the fifth administration interval commences 2 to 4 days, more preferably 3 days after initiation of the fourth administration interval.

Alternatively, after said fifth administration interval, the titration phase may continue, i.e. Cebranopadol is administered at a sixth daily dose for a sixth administration interval. At this stage the sixth daily dose of Cebranopadol may be either further increased or decreased, depending on the individual needs of the subject.

Therefore, in a preferred embodiment, Cebranopadol is administered according to an administration regimen comprising the preferred fifth administration interval described above and additionally comprising (iv) a sixth administration interval, which lasts for at least 1 day, preferably for at least 2 consecutive days and directly follows the fifth administration interval without interruption, wherein a sixth daily dose of Cebranopadol is administered on every day of the sixth administration interval;

wherein the fifth daily dose of Cebranopadol is lower than the sixth daily dose of Cebranopadol.

The sixth administration interval directly follows the fifth administration interval without interruption.

Preferably, the sixth administration interval, independent of any preceding or subsequent administration intervals, lasts for 2 to 6 consecutive days; more preferably 2 to 5 consecutive days; still more preferably 2 to 4 consecutive days; even more preferably 3 consecutive days.

Preferably, the sixth daily dose of Cebranopadol is within the range of from 410 to 590 μg, more preferably 420 to 580 μg, still more preferably 430 to 570 μg, yet more preferably 440 to 560 μg, even more preferably 450 to 550 μg, most preferably 460 to 540 μg, and in particular 470 to 530 μg. Preferred sixth daily doses of Cebranopadol include but are not limited to about 450 μg, about 475 μg, about 500 μg, about 525 μg, and about 550 μg.

Preferably, on any day of the sixth administration interval, Cebranopadol is administered at the same administration frequency, which may be once daily (sid) or twice daily (bid), whereas administration once daily (sid) is particularly preferred.

When the sixth daily dose of Cebranopadol is administered twice daily, said sixth daily dose is preferably divided into two portions of approximately or exactly the same size, wherein one portion is administered during the day, e.g. in the morning, and the other portion is administered during the same day but after several hours, preferably after about 12 hours, e.g. in the evening.

The sixth daily dose of Cebranopadol may be administered orally, buccally, sublingually, transmucosally, intralumbally, intraperitoneally, transdermally, intravenously, intramusculously, intragluteally, intracutaneously or subcutaneously, orally being most preferred.

When Cebranopadol is administered according to an administration regimen additionally comprising a sixth administration interval, the fifth daily dose of Cebranopadol is lower than the sixth daily dose of Cebranopadol.

Preferably, the first daily dose of Cebranopadol is within the range of from 2.5 to 17.5 wt.-% of the sixth daily dose of Cebranopadol, more preferably from 5.0 to 15 wt.-%, still more preferably from 7.5 to 12.5 wt.-%; and/or the second daily dose of Cebranopadol is within the range of from 10 to 30 wt.-% of the sixth daily dose of Cebranopadol, more preferably from 12.5 to 27.5 wt.-%, still more preferably from 15 to 25 wt.-%, most preferably from 17.5 to 22.5 wt.-%; and/or the third daily dose of Cebranopadol is within the range of from 20 to 60 wt.-% of the sixth daily dose of Cebranopadol, more preferably from 25 to 55 wt.-%, still more preferably from 30 to 50 wt.-%, most preferably from 35 to 45 wt.-%; and/or the fourth daily dose of Cebranopadol is within the range of from 40 to 80 wt.-% of the sixth daily dose of Cebranopadol, more preferably from 45 to 75 wt.-%, still more preferably from 50 to 70 wt.-%, most preferably from 55 to 65 wt.-%; and/or the fifth daily dose of Cebranopadol is within the range of from 60 to 97.5 wt.-% of the sixth daily dose of Cebranopadol, more preferably from 65 to 95 wt.-%, still more preferably from 70 to 90 wt.-%, most preferably from 75 to 85 wt.-%.

After said sixth administration interval, the titration phase may be terminated, i.e. administration of Cebranopadol may be continued at the sixth daily dose, thereby initiating the continuous phase.

Accordingly, in a preferred embodiment, the administration regimen is hexaphasic (6 consecutive administration intervals). Preferably, said hexaphasic administration regimen comprises at least 4, at least 5, at least 6, at least 7, at least 8, at least 9, at least 10, at least 11, at least 12, at least 13, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, or at least 28 days; the first daily dose of Cebranopadol during the first administration interval is within the range of from 25 μg±5% to 75 μg±5%, preferably administered orally once daily (sid); the second daily dose of Cebranopadol during the second administration interval is within the range of from 50 μg±5% to 150 μg±5%, preferably administered orally once daily (sid); the third daily dose of Cebranopadol during the third administration interval is within the range of from 150 μg±5% to 250 μg±5%, preferably administered orally once daily (sid); the fourth daily dose of Cebranopadol during the fourth administration interval is within the range of from 250 μg±5% to 350 μg±5%, preferably administered orally once daily (sid); the fifth daily dose of Cebranopadol during the fifth administration interval is within the range of from 350 μg±5% to 450 μg±5%, preferably administered orally once daily (sid); and the sixth daily dose of Cebranopadol during the sixth administration interval is within the range of from 450 μg±5% to 550 μg±5%, preferably administered orally once daily (sid). Preferably, the second administration interval commences 2 to 4 days, more preferably 3 days after initiation of administration of Cebranopadol with the first administration interval, the third administration interval commences 2 to 4 days, more preferably 3 days after initiation of the second administration interval, and the fourth administration interval commences 2 to 4 days, more preferably 3 days after initiation of the third administration interval, and the fifth administration interval commences 2 to 4 days, more preferably 3 days after initiation of the fourth administration interval, and the sixth administration interval commences 2 to 4 days, more preferably 3 days after initiation of the fifth administration interval.

Alternatively, after said sixth administration interval, the titration phase may continue, i.e. Cebranopadol is administered at a seventh daily dose for a seventh administration interval. At this stage the seventh daily dose of Cebranopadol may be either further increased or decreased, depending on the individual needs of the subject.

Therefore, in a preferred embodiment, Cebranopadol is administered according to an administration regimen comprising the preferred sixth administration interval described above and additionally comprising (iv) a seventh administration interval, which lasts for at least 1 day, preferably for at least 2 consecutive days and directly follows the sixth administration interval without interruption, wherein a seventh daily dose of Cebranopadol is administered on every day of the seventh administration interval;

wherein the sixth daily dose of Cebranopadol is lower than the seventh daily dose of Cebranopadol.

The seventh administration interval directly follows the sixth administration interval without interruption.

Preferably, the seventh administration interval, independent of any preceding or subsequent administration intervals, lasts for 2 to 6 consecutive days; more preferably 2 to 5 consecutive days; still more preferably 2 to 4 consecutive days; even more preferably 3 consecutive days.

Preferably, the seventh daily dose of Cebranopadol is within the range of from 510 to 690 µg, more preferably 520 to 680 µg, still more preferably 530 to 670 µg, yet more preferably 540 to 660 µg, even more preferably 550 to 650 µg, most preferably 560 to 640 µg, and in particular 570 to 630 µg. Preferred seventh daily doses of Cebranopadol include but are not limited to about 550 µg, about 575 µg, about 600 µg, about 625 µg, and about 650 µg.

Preferably, on any day of the seventh administration interval, Cebranopadol is administered at the same administration frequency, which may be once daily (sid) or twice daily (bid), whereas administration once daily (sid) is particularly preferred.

When the seventh daily dose of Cebranopadol is administered twice daily, said seventh daily dose is preferably divided into two portions of approximately or exactly the same size, wherein one portion is administered during the day, e.g. in the morning, and the other portion is administered during the same day but after several hours, preferably after about 12 hours, e.g. in the evening.

The seventh daily dose of Cebranopadol may be administered orally, buccally, sublingually, transmucosally, intralumbally, intraperitoneally, transdermally, intravenously, intramusculously, intragluteally, intracutaneously or subcutaneously, orally being most preferred.

When Cebranopadol is administered according to an administration regimen additionally comprising a seventh administration interval, the sixth daily dose of Cebranopadol is lower than the seventh daily dose of Cebranopadol.

Preferably, the first daily dose of Cebranopadol is within the range of from 4.0 to 12 wt.-% of the seventh daily dose of Cebranopadol, more preferably from 5.0 to 11 wt.-%, still more preferably from 6.0 to 10 wt.-%; and/or the second daily dose of Cebranopadol is within the range of from 9.0 to 26 wt.-% of the seventh daily dose of Cebranopadol, more preferably from 11 to 24 wt.-%, still more preferably from 13 to 22 wt.-%, most preferably from 15 to 20 wt.-%; and/or the third daily dose of Cebranopadol is within the range of from 15 to 50 wt.-% of the seventh daily dose of Cebranopadol, more preferably from 20 to 45 wt.-%, still more preferably from 25 to 40 wt.-%, most preferably from 30 to 35 wt.-%; and/or the fourth daily dose of Cebranopadol is within the range of from 30 to 70 wt.-% of the seventh daily dose of Cebranopadol, more preferably from 35 to 65 wt.-%, still more preferably from 40 to 60 wt.-%, most preferably from 45 to 55 wt.-%; and/or the fifth daily dose of Cebranopadol is within the range of from 50 to 85 wt.-% of the seventh daily dose of Cebranopadol, more preferably from 55 to 80 wt.-%, still more preferably from 60 to 75 wt.-%, most preferably from 65 to 70 wt.-%; and/or the sixth daily dose of Cebranopadol is within the range of from 65 to 97.5 wt.-% of the seventh daily dose of Cebranopadol, more preferably from 70 to 95 wt.-%, still more preferably from 75 to 90 wt.-%, most preferably from 80 to 85 wt.-%.

After said seventh administration interval, the titration phase may be terminated, i.e. administration of Cebranopadol may be continued at the seventh daily dose, thereby initiating the continuous phase.

Accordingly, in a preferred embodiment, the administration regimen is heptaphasic (7 consecutive administration intervals). Preferably, said heptaphasic administration regimen comprises at least 4, at least 5, at least 6, at least 7, at least 8, at least 9, at least 10, at least 11, at least 12, at least 13, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, or at least 28 days; the first daily dose of Cebranopadol during the first administration interval is within the range of from 25 µg±5% to 75 µg±5%, preferably administered orally once daily (sid); the second daily dose of Cebranopadol during the second administration interval is within the range of from 50 µg±5% to 150 µg±5%, preferably administered orally once daily (sid); the third daily dose of Cebranopadol during the third administration interval is within the range of from 150 µg±5% to 250 µg±5%, preferably administered orally once daily (sid); the fourth daily dose of Cebranopadol during the fourth administration interval is within the range of from 250 µg±5% to 350 µg±5%, preferably administered orally once daily (sid); the fifth daily dose of Cebranopadol during the fifth administration interval is within the range of from 350 µg±5% to 450 µg±5%, preferably administered orally once daily (sid); and the sixth daily dose of Cebranopadol during the sixth administration interval is within the range of from 450 µg±5% to 550 µg±5%, preferably administered orally once daily (sid), and the seventh daily dose of Cebranopadol during the seventh administration interval is within the range of from 550 µg±5% to 650 µg±5%, preferably administered orally once daily (sid). Preferably, the second administration interval commences 2 to 4 days, more preferably 3 days after initiation of administration of Cebranopadol with the first administration interval, the third administration interval commences 2 to 4 days, more preferably 3 days after initiation of the second administration interval, and the fourth administration interval commences 2 to 4 days, more preferably 3 days after initiation of the third administration interval, and the fifth administration interval commences 2 to 4 days, more preferably 3 days after initiation of the fourth administration interval, and the sixth administration interval commences 2 to 4 days, more preferably 3 days after initiation of the fifth administration interval, and the seventh administration interval commences 2 to 4 days, more preferably 3 days after initiation of the sixth administration interval.

In preferred embodiments, the first daily dose of Cebranopadol, the second daily dose of Cebranopadol, the optional third daily dose of Cebranopadol, and/or the optional fourth daily dose of Cebranopadol, and/or the optional fifth daily dose of Cebranopadol, and/or the optional sixth daily dose of Cebranopadol, and/or the optional seventh daily dose of Cebranopadol independently of one another are administered orally.

In preferred embodiments, the first daily dose of Cebranopadol, the second daily dose of Cebranopadol, the optional third daily dose of Cebranopadol, and/or the optional fourth daily dose of Cebranopadol, and/or the optional fifth daily dose of Cebranopadol, and/or the optional sixth daily dose of Cebranopadol, and/or the optional seventh daily dose of Cebranopadol independently of one another are administered once daily (sid), preferably approximately at the same time of every day. Preferably, first daily dose of Cebranopadol, the second daily dose of Cebranopadol, the optional third daily dose of Cebranopadol, the optional fourth daily dose of Cebranopadol, the optional fifth daily dose of Cebranopadol, the optional sixth daily dose of Cebranopadol, as well as the optional seventh daily dose of Cebranopadol are administered each once daily (sid), preferably approximately at the same time of every day.

In preferred embodiments, the first administration interval, the second administration interval, the optional third administration interval, and/or the optional fourth administration interval, and/or the optional fifth administration interval, and/or the optional sixth administration interval, and/or the optional seventh administration interval independently of one another last for at least 3 consecutive days; more preferably at least 4 consecutive days; still more preferably at least 5 consecutive days; even more preferably from 3 to 14 consecutive days, preferably from 3 to 10 consecutive days, more preferably from 3 to 7 consecutive days; most preferably from 5 to 11 consecutive days; and in particular from 5 to 7 consecutive days. In other preferred embodiments, the first administration interval, the second administration interval, the optional third administration interval, and/or the optional fourth administration interval, and/or the optional fifth administration interval, and/or the optional sixth administration interval, and/or the optional seventh administration interval independently of one another last for 2 to 4 consecutive days, preferably 3 consecutive days. Preferably, the first administration interval, the second administration interval, the optional third administration interval, and/or the optional fourth administration interval, and/or the optional fifth administration interval, and/or the optional sixth administration interval, and/or the optional seventh administration interval each last for the same period of time.

In preferred embodiments, the administration regimen according to the invention comprises
- (i) a first administration interval, which lasts for at least $\alpha$ consecutive days, wherein a first daily dose of Cebranopadol is orally administered on every day of the first administration interval;
- (ii) a second administration interval, which lasts for at least $\beta$ consecutive days and directly follows the first administration interval without interruption, wherein a second daily dose of Cebranopadol is orally administered on every day of the second administration interval;
- (iii) a third administration interval, which lasts for at least $\gamma$ consecutive days and directly follows the second administration interval without interruption, wherein a third daily dose of Cebranopadol is orally administered on every day of the third administration interval;
- (iv) optionally, a fourth administration interval, which lasts for at least $\delta$ consecutive days and directly follows the third administration interval without interruption, wherein a fourth daily dose of Cebranopadol is orally administered on every day of the fourth administration interval;
- (v) optionally, a fifth administration interval, which lasts for at least $\varepsilon$ consecutive days and directly follows the fourth administration interval without interruption, wherein a fifth daily dose of Cebranopadol is orally administered on every day of the fifth administration interval;
- (vi) optionally, a sixth administration interval, which lasts for at least $\varphi$ consecutive days and directly follows the fifth administration interval without interruption, wherein a sixth daily dose of Cebranopadol is orally administered on every day of the sixth administration interval; and
- (vii) optionally, a seventh administration interval, which lasts for at least $\chi$ consecutive days and directly follows the sixth administration interval without interruption, wherein a seventh daily dose of Cebranopadol is orally administered on every day of the seventh administration interval;

and satisfies any of the following requirements $A_1$ to $C_7$:

|  | $A_1$ | $A_2$ | $A_3$ | $A_4$ | $A_5$ | $A_6$ | $A_7$ |
|---|---|---|---|---|---|---|---|
| first daily dose [µg] | 100 ± 80 | 100 ± 80 | 100 ± 80 | 100 ± 80 | 100 ± 80 | 100 ± 80 | 100 ± 80 |
| $\alpha$ [days] | ≥3 | ≥4 | ≥5 | ≥6 | 7 ± 3 | 6 ± 2 | 6 ± 1 |
| second daily dose [µg] | 200 ± 80 | 200 ± 80 | 200 ± 80 | 200 ± 80 | 200 ± 80 | 200 ± 80 | 200 ± 80 |
| $\beta$ [days] | ≥3 | ≥4 | ≥5 | ≥6 | 7 ± 3 | 6 ± 2 | 6 ± 1 |
| third daily dose [µg] | 400 ± 80 | 400 ± 80 | 400 ± 80 | 400 ± 80 | 400 ± 80 | 400 ± 80 | 400 ± 80 |
| $\gamma$ [days] | ≥3 | ≥4 | ≥5 | ≥6 | 7 ± 3 | 6 ± 2 | 6 ± 1 |

|  | $A_8$ | $A_9$ | $A_{10}$ | $A_{11}$ | $A_{12}$ | $A_{13}$ | $A_{14}$ |
|---|---|---|---|---|---|---|---|
| first daily dose [µg] | 100 ± 50 | 100 ± 50 | 100 ± 50 | 100 ± 50 | 100 ± 50 | 100 ± 50 | 100 ± 50 |
| $\alpha$ [days] | ≥3 | ≥4 | ≥5 | ≥6 | 7 ± 3 | 6 ± 2 | 6 ± 1 |
| second daily dose [µg] | 200 ± 50 | 200 ± 50 | 200 ± 50 | 200 ± 50 | 200 ± 50 | 200 ± 50 | 200 ± 50 |
| $\beta$ [days] | ≥3 | ≥4 | ≥5 | ≥6 | 7 ± 3 | 6 ± 2 | 6 ± 1 |
| third daily dose [µg] | 400 ± 50 | 400 ± 50 | 400 ± 50 | 400 ± 50 | 400 ± 50 | 400 ± 50 | 400 ± 50 |
| $\gamma$ [days] | ≥3 | ≥4 | ≥5 | ≥6 | 7 ± 3 | 6 ± 2 | 6 ± 1 |

|  | $A_{15}$ | $A_{16}$ | $A_{17}$ | $A_{18}$ | $A_{19}$ | $A_{20}$ | $A_{21}$ |
|---|---|---|---|---|---|---|---|
| first daily dose [µg] | 100 ± 20 | 100 ± 20 | 100 ± 20 | 100 ± 20 | 100 ± 20 | 100 ± 20 | 100 ± 20 |
| $\alpha$ [days] | ≥3 | ≥4 | ≥5 | ≥6 | 7 ± 3 | 6 ± 2 | 6 ± 1 |
| second daily dose [µg] | 200 ± 20 | 200 ± 20 | 200 ± 20 | 200 ± 20 | 200 ± 20 | 200 ± 20 | 200 ± 20 |

-continued

|  | | | | | | | |
|---|---|---|---|---|---|---|---|
| β [days] | ≥3 | ≥4 | ≥5 | ≥6 | 7 ± 3 | 6 ± 2 | 6 ± 1 |
| third daily dose [µg] | 400 ± 20 | 400 ± 20 | 400 ± 20 | 400 ± 20 | 400 ± 20 | 400 ± 20 | 400 ± 20 |
| γ [days] | ≥3 | ≥4 | ≥5 | ≥6 | 7 ± 3 | 6 ± 2 | 6 ± 1 |

|  | $B_1$ | $B_2$ | $B_3$ | $B_4$ | $B_5$ | $B_6$ | $B_7$ |
|---|---|---|---|---|---|---|---|
| first daily dose [µg] | 100 ± 80 | 100 ± 80 | 100 ± 80 | 100 ± 80 | 100 ± 80 | 100 ± 80 | 100 ± 80 |
| α [days] | ≥3 | ≥4 | ≥5 | ≥6 | 7 ± 3 | 6 ± 2 | 6 ± 1 |
| second daily dose [µg] | 200 ± 80 | 200 ± 80 | 200 ± 80 | 200 ± 80 | 200 ± 80 | 200 ± 80 | 200 ± 80 |
| β [days] | ≥3 | ≥4 | ≥5 | ≥6 | 7 ± 3 | 6 ± 2 | 6 ± 1 |
| third daily dose [µg] | 400 ± 80 | 400 ± 80 | 400 ± 80 | 400 ± 80 | 400 ± 80 | 400 ± 80 | 400 ± 80 |
| γ [days] | ≥3 | ≥4 | ≥5 | ≥6 | 7 ± 3 | 6 ± 2 | 6 ± 1 |
| fourth daily dose [µg] | 600 ± 80 | 600 ± 80 | 600 ± 80 | 600 ± 80 | 600 ± 80 | 600 ± 80 | 600 ± 80 |
| δ [days] | ≥3 | ≥4 | ≥5 | ≥6 | 7 ± 3 | 6 ± 2 | 6 ± 1 |

|  | $B_8$ | $B_9$ | $B_{10}$ | $B_{11}$ | $B_{12}$ | $B_{13}$ | $B_{14}$ |
|---|---|---|---|---|---|---|---|
| first daily dose [µg] | 100 ± 50 | 100 ± 50 | 100 ± 50 | 100 ± 50 | 100 ± 50 | 100 ± 50 | 100 ± 50 |
| α [days] | ≥3 | ≥4 | ≥5 | ≥6 | 7 ± 3 | 6 ± 2 | 6 ± 1 |
| second daily dose [µg] | 200 ± 50 | 200 ± 50 | 200 ± 50 | 200 ± 50 | 200 ± 50 | 200 ± 50 | 200 ± 50 |
| β [days] | ≥3 | ≥4 | ≥5 | ≥6 | 7 ± 3 | 6 ± 2 | 6 ± 1 |
| third daily dose [µg] | 400 ± 50 | 400 ± 50 | 400 ± 50 | 400 ± 50 | 400 ± 50 | 400 ± 50 | 400 ± 50 |
| γ [days] | ≥3 | ≥4 | ≥5 | ≥6 | 7 ± 3 | 6 ± 2 | 6 ± 1 |
| fourth daily dose [µg] | 600 ± 50 | 600 ± 50 | 600 ± 50 | 600 ± 50 | 600 ± 50 | 600 ± 50 | 600 ± 50 |
| δ [days] | ≥3 | ≥4 | ≥5 | ≥6 | 7 ± 3 | 6 ± 2 | 6 ± 1 |

|  | $B_{15}$ | $B_{16}$ | $B_{17}$ | $B_{18}$ | $B_{19}$ | $B_{20}$ | $B_{21}$ |
|---|---|---|---|---|---|---|---|
| first daily dose [µg] | 100 ± 20 | 100 ± 20 | 100 ± 20 | 100 ± 20 | 100 ± 20 | 100 ± 20 | 100 ± 20 |
| α [days] | ≥3 | ≥4 | ≥5 | ≥6 | 7 ± 3 | 6 ± 2 | 6 ± 1 |
| second daily dose [µg] | 200 ± 20 | 200 ± 20 | 200 ± 20 | 200 ± 20 | 200 ± 20 | 200 ± 20 | 200 ± 20 |
| β [days] | ≥3 | ≥4 | ≥5 | ≥6 | 7 ± 3 | 6 ± 2 | 6 ± 1 |
| third daily dose [µg] | 400 ± 20 | 400 ± 20 | 400 ± 20 | 400 ± 20 | 400 ± 20 | 400 ± 20 | 400 ± 20 |
| γ [days] | ≥3 | ≥4 | ≥5 | ≥6 | 7 ± 3 | 6 ± 2 | 6 ± 1 |
| fourth daily dose [µg] | 600 ± 20 | 600 ± 20 | 600 ± 20 | 600 ± 20 | 600 ± 20 | 600 ± 20 | 600 ± 20 |
| δ [days] | ≥3 | ≥4 | ≥5 | ≥6 | 7 ± 3 | 6 ± 2 | 6 ± 1 |

|  | $B_{22}$ | $B_{23}$ |
|---|---|---|
| first daily dose [µg] | 100 | 100 |
| α [days] | 6 | 7 |
| second daily dose [µg] | 200 | 200 |
| β [days] | 6 | 7 |
| third daily dose [µg] | 400 | 400 |
| γ [days] | 6 | 7 |
| fourth daily dose [µg] | 600 | 600 |
| δ [days] | ≥2 | ≥2 |

|  | $C_1$ | $C_2$ | $C_3$ | $C_4$ | $C_5$ | $C_6$ | $C_7$ |
|---|---|---|---|---|---|---|---|
| first daily dose [µg] | 50 ± 40 | 50 ± 40 | 50 ± 40 | 50 ± 20 | 50 ± 20 | 50 ± 20 | 50 |
| α [days] | ≥2 | ≥3 | 3 ± 1 | ≥2 | ≥3 | 3 ± 1 | 3 |
| second daily dose [µg] | 100 ± 80 | 100 ± 80 | 100 ± 80 | 100 ± 40 | 100 ± 40 | 100 ± 40 | 100 |
| β [days] | ≥2 | ≥3 | 3 ± 1 | ≥2 | ≥3 | 3 ± 1 | 3 |
| third daily dose [µg] | 200 ± 80 | 200 ± 80 | 200 ± 80 | 200 ± 40 | 200 ± 40 | 200 ± 40 | 200 |
| γ [days] | ≥2 | ≥3 | 3 ± 1 | ≥2 | ≥3 | 3 ± 1 | 3 |
| fourth daily dose [µg] | 300 ± 80 | 300 ± 80 | 300 ± 80 | 300 ± 40 | 300 ± 40 | 300 ± 40 | 300 |
| δ [days] | ≥2 | ≥3 | 3 ± 1 | ≥2 | ≥3 | 3 ± 1 | 3 |
| fifth daily dose [µg] | 400 ± 80 | 400 ± 80 | 400 ± 80 | 400 ± 40 | 400 ± 40 | 400 ± 40 | 400 |
| ε [days] | ≥2 | ≥3 | 3 ± 1 | ≥2 | ≥3 | 3 ± 1 | 3 |
| sixth daily dose [µg] | 500 ± 80 | 500 ± 80 | 500 ± 80 | 500 ± 40 | 500 ± 40 | 500 ± 40 | 500 |
| φ [days] | ≥2 | ≥3 | 3 ± 1 | ≥2 | ≥3 | 3 ± 1 | 3 |
| seventh daily dose [µg] | 600 ± 80 | 600 ± 80 | 600 ± 80 | 600 ± 40 | 600 ± 40 | 600 ± 40 | 600 |
| χ [days] | ≥2 | ≥3 | 3 ± 1 | ≥2 | ≥3 | 3 ± 1 | ≥2 |

Thus, embodiment $A_{19}$ means for example that the administration regimen according to the invention comprises
  (i) a first administration interval, which lasts for 4 to 10 consecutive days (7±3 days), wherein a first daily dose of Cebranopadol amounting to 80-120 µg (100±20 µg) is orally administered on every day of the 4 to 10 consecutive days of the first administration interval;
  (ii) a second administration interval, which lasts for 4 to 10 consecutive days (7±3 days) and directly follows the first administration interval without interruption, wherein a second daily dose of Cebranopadol amounting to 180-220 µg (200±20 µg) is orally administered on every day of the 4 to 10 consecutive days of the second administration interval; and
  (iii) a third administration interval, which lasts for 4 to 10 consecutive days (7±3 days) and directly follows the second administration interval without interruption, wherein a third daily dose of Cebranopadol amounting to 380-420 µg (400±20 µg) is orally administered on every day of the 4 to 10 consecutive days of the third administration interval.

Preferably, Cebranopadol is administered once daily (sid) or twice daily (bid), whereas administration once daily (sid) is particularly preferred. Preferably, the number of administrations per day is harmonized, i.e. when during the first administration interval Cebranopadol is administered once daily (sid), during the second administration interval Cebranopadol is preferably also administered once daily (sid). The same applies to the optional third administration interval and the optional fourth administration interval and the optional fifth administration interval and the optional sixth administration interval and the optional seventh administration interval.

Preferably, Cebranopadol is administered orally. Preferably, the route of administration is harmonized, i.e. when during the first administration interval Cebranopadol is administered orally, during the second administration interval Cebranopadol is preferably also administered orally. The same applies to the optional third administration interval and the optional fourth administration interval and the optional fifth administration interval and the optional sixth administration interval and the optional seventh administration interval.

The administration regimen may be static (forced) or dynamic.

In a particularly preferred embodiment subjects initiate treatment with Cebranopadol, orally administered once daily (sid), at a first daily dose of 100 µg±5%. After 5 to 7 days the first daily dose is increased to a second daily dose amounting to 200 µg±5%. This is the minimum dose to be continued with. To the discretion of the subject, upward titration may then occur at a minimum of 5 to 7 days intervals in increments of 100 µg±5% or in increments of 200 µg±5%. To the discretion of the subject, downward titration (preferably not below the minimum dose) is also permitted using the same decrements without a time restriction.

In another particularly preferred embodiment subjects initiate treatment with Cebranopadol, orally administered once daily (sid), at a first daily dose of 50 µg±5%. After 2 to 4 days the first daily dose is increased to a second daily dose amounting to 100 µg±5%. This is the minimum dose to be continued with. To the discretion of the subject, upward titration may then occur at a minimum of 2 to 4 days intervals in increments of 50 µg±5% or in increments of 100 µg±5% or in increments of 200 µg±5%. To the discretion of the subject, downward titration (preferably not below the minimum dose) is also permitted using the same decrements without a time restriction.

The titration of Cebranopadol is effective in reducing discontinuations due to adverse effects while maintaining the analgesic properties of the compound. This is particularly true in the case of patients who previously had difficulty tolerating an analgesic because of side effects such as dizziness, nausea and vomiting. This result is based on the cumulative proportion of patients who discontinued use of the agent due to adverse side effects.

Cebranopadol according to the invention is for use in the treatment of pain.

Preferably, Cebranopadol according to the invention is for use in the treatment of pain, whereby the incidence of adverse events is reduced.

Preferably, the pain is
  acute pain or chronic pain; and/or
  nociceptive pain or neuropathic pain; and/or
  postoperative pain, malignant pain, and/or inflammatory pain.

Preferred types of pain that are treated according to the invention include but are not limited to pain due to diabetic neuropathy, pain due to peripheral neuropathy, pain due to postherpetic neuralgia, pain due to fibromyalgia, low back pain, pain due to osteoarthritis, visceral pain, musculoskeletal pain, and the like.

Another aspect of the invention relates to a method for treating pain in a subject in need thereof, typically a human, comprising administering Cebranopadol according to the administration regimen of the invention as described above.

Another aspect of the invention relates to the use of Cebranopadol for the manufacture of medicaments for administration according to the administration regimen of the invention as described above.

Another aspect of the invention relates to a kit comprising a multitude of administration units that are useful for administering Cebranopadol according to the administration regimen of the invention as described above.

Preferably, the kit comprises
a multitude of at least α administration units A each containing a first daily dose of Cebranopadol, that are adapted to be orally administered once daily (sid) during a first administration interval;
a multitude of at least β administration units B each containing a second daily dose of Cebranopadol, that are adapted to be orally administered once daily (sid) during a second administration interval directly following the first administration interval without interruption;
a multitude of at least γ administration units C each containing a third daily dose of Cebranopadol, that are adapted to be orally administered once daily (sid) during a third administration interval directly following the second administration interval without interruption; and
optionally, a multitude of at least δ administration units D each containing a fourth daily dose of Cebranopadol, that are adapted to be orally administered once daily (sid) during a fourth administration interval directly following the third administration interval without interruption,
optionally, a multitude of at least ε administration units E each containing a fifth daily dose of Cebranopadol, that are adapted to be orally administered once daily (sid) during a fifth administration interval directly following the fourth administration interval without interruption,
optionally, a multitude of at least φ administration units F each containing a sixth daily dose of Cebranopadol, that are adapted to be orally administered once daily (sid) during a sixth administration interval directly following the fifth administration interval without interruption,
optionally, a multitude of at least χ administration units G each containing a seventh daily dose of Cebranopadol, that are adapted to be orally administered once daily (sid) during a seventh administration interval directly following the sixth administration interval without interruption,
wherein the kit satisfies any of the following requirements $A_1$ to $C_7$:

|  | $A_1$ | $A_2$ | $A_3$ | $A_4$ | $A_5$ | $A_6$ | $A_7$ |
|---|---|---|---|---|---|---|---|
| first daily dose [µg] | 100 ± 80 | 100 ± 80 | 100 ± 80 | 100 ± 80 | 100 ± 80 | 100 ± 80 | 100 ± 80 |
| α [number of administration units A] | ≥3 | ≥4 | ≥5 | ≥6 | 7 ± 3 | 6 ± 2 | 6 ± 1 |
| second daily dose [µg] | 200 ± 80 | 200 ± 80 | 200 ± 80 | 200 ± 80 | 200 ± 80 | 200 ± 80 | 200 ± 80 |
| β [number of administration units B] | ≥3 | ≥4 | ≥5 | ≥6 | 7 ± 3 | 6 ± 2 | 6 ± 1 |
| third daily dose [µg] | 400 ± 80 | 400 ± 80 | 400 ± 80 | 400 ± 80 | 400 ± 80 | 400 ± 80 | 400 ± 80 |
| γ [number of administration units C] | ≥3 | ≥4 | ≥5 | ≥6 | 7 ± 3 | 6 ± 2 | 6 ± 1 |

|  | $A_8$ | $A_9$ | $A_{10}$ | $A_{11}$ | $A_{12}$ | $A_{13}$ | $A_{14}$ |
|---|---|---|---|---|---|---|---|
| first daily dose [µg] | 100 ± 50 | 100 ± 50 | 100 ± 50 | 100 ± 50 | 100 ± 50 | 100 ± 50 | 100 ± 50 |
| α [number of administration units A] | ≥3 | ≥4 | ≥5 | ≥6 | 7 ± 3 | 6 ± 2 | 6 ± 1 |
| second daily dose [µg] | 200 ± 50 | 200 ± 50 | 200 ± 50 | 200 ± 50 | 200 ± 50 | 200 ± 50 | 200 ± 50 |
| β [number of administration units B] | ≥3 | ≥4 | ≥5 | ≥6 | 7 ± 3 | 6 ± 2 | 6 ± 1 |
| third daily dose [µg] | 400 ± 50 | 400 ± 50 | 400 ± 50 | 400 ± 50 | 400 ± 50 | 400 ± 50 | 400 ± 50 |
| γ [number of administration units C] | ≥3 | ≥4 | ≥5 | ≥6 | 7 ± 3 | 6 ± 2 | 6 ± 1 |

|  | $A_{15}$ | $A_{16}$ | $A_{17}$ | $A_{18}$ | $A_{19}$ | $A_{20}$ | $A_{21}$ |
|---|---|---|---|---|---|---|---|
| first daily dose [µg] | 100 ± 20 | 100 ± 20 | 100 ± 20 | 100 ± 20 | 100 ± 20 | 100 ± 20 | 100 ± 20 |
| α [number of administration units A] | ≥3 | ≥4 | ≥5 | ≥6 | 7 ± 3 | 6 ± 2 | 6 ± 1 |
| second daily dose [µg] | 200 ± 20 | 200 ± 20 | 200 ± 20 | 200 ± 20 | 200 ± 20 | 200 ± 20 | 200 ± 20 |
| β [number of administration units B] | ≥3 | ≥4 | ≥5 | ≥6 | 7 ± 3 | 6 ± 2 | 6 ± 1 |
| third daily dose [µg] | 400 ± 20 | 400 ± 20 | 400 ± 20 | 400 ± 20 | 400 ± 20 | 400 ± 20 | 400 ± 20 |
| γ [number of administration units C] | ≥3 | ≥4 | ≥5 | ≥6 | 7 ± 3 | 6 ± 2 | 6 ± 1 |

|  | $B_1$ | $B_2$ | $B_3$ | $B_4$ | $B_5$ | $B_6$ | $B_7$ |
|---|---|---|---|---|---|---|---|
| first daily dose [µg] | 100 ± 80 | 100 ± 80 | 100 ± 80 | 100 ± 80 | 100 ± 80 | 100 ± 80 | 100 ± 80 |
| α [number of administration units A] | ≥3 | ≥4 | ≥5 | ≥6 | 7 ± 3 | 6 ± 2 | 6 ± 1 |
| second daily dose [µg] | 200 ± 80 | 200 ± 80 | 200 ± 80 | 200 ± 80 | 200 ± 80 | 200 ± 80 | 200 ± 80 |
| β [number of administration units B] | ≥3 | ≥4 | ≥5 | ≥6 | 7 ± 3 | 6 ± 2 | 6 ± 1 |
| third daily dose [µg] | 400 ± 80 | 400 ± 80 | 400 ± 80 | 400 ± 80 | 400 ± 80 | 400 ± 80 | 400 ± 80 |
| γ [number of administration units C] | ≥3 | ≥4 | ≥5 | ≥6 | 7 ± 3 | 6 ± 2 | 6 ± 1 |
| fourth daily dose [µg] | 600 ± 80 | 600 ± 80 | 600 ± 80 | 600 ± 80 | 600 ± 80 | 600 ± 80 | 600 ± 80 |
| δ [number of administration units D] | ≥3 | ≥4 | ≥5 | ≥6 | 7 ± 3 | 6 ± 2 | 6 ± 1 |

|  | $B_8$ | $B_9$ | $B_{10}$ | $B_{11}$ | $B_{12}$ | $B_{13}$ | $B_{14}$ |
|---|---|---|---|---|---|---|---|
| first daily dose [µg] | 100 ± 50 | 100 ± 50 | 100 ± 50 | 100 ± 50 | 100 ± 50 | 100 ± 50 | 100 ± 50 |
| α [number of administration units A] | ≥3 | ≥4 | ≥5 | ≥6 | 7 ± 3 | 6 ± 2 | 6 ± 1 |
| second daily dose [µg] | 200 ± 50 | 200 ± 50 | 200 ± 50 | 200 ± 50 | 200 ± 50 | 200 ± 50 | 200 ± 50 |
| β [number of administration units B] | ≥3 | ≥4 | ≥5 | ≥6 | 7 ± 3 | 6 ± 2 | 6 ± 1 |
| third daily dose [µg] | 400 ± 50 | 400 ± 50 | 400 ± 50 | 400 ± 50 | 400 ± 50 | 400 ± 50 | 400 ± 50 |
| γ [number of administration units C] | ≥3 | ≥4 | ≥5 | ≥6 | 7 ± 3 | 6 ± 2 | 6 ± 1 |
| fourth daily dose [µg] | 600 ± 50 | 600 ± 50 | 600 ± 50 | 600 ± 50 | 600 ± 50 | 600 ± 50 | 600 ± 50 |
| δ [number of administration units D] | ≥3 | ≥4 | ≥5 | ≥6 | 7 ± 3 | 6 ± 2 | 6 ± 1 |

|  | $B_{15}$ | $B_{16}$ | $B_{17}$ | $B_{18}$ | $B_{19}$ | $B_{20}$ | $B_{21}$ |
|---|---|---|---|---|---|---|---|
| first daily dose [µg] | 100 ± 20 | 100 ± 20 | 100 ± 20 | 100 ± 20 | 100 ± 20 | 100 ± 20 | 100 ± 20 |
| α [number of administration units A] | ≥3 | ≥4 | ≥5 | ≥6 | 7 ± 3 | 6 ± 2 | 6 ± 1 |
| second daily dose [µg] | 200 ± 20 | 200 ± 20 | 200 ± 20 | 200 ± 20 | 200 ± 20 | 200 ± 20 | 200 ± 20 |
| β [number of administration units B] | ≥3 | ≥4 | ≥5 | ≥6 | 7 ± 3 | 6 ± 2 | 6 ± 1 |
| third daily dose [µg] | 400 ± 20 | 400 ± 20 | 400 ± 20 | 400 ± 20 | 400 ± 20 | 400 ± 20 | 400 ± 20 |

-continued

| | | | | | | | |
|---|---|---|---|---|---|---|---|
| γ [number of administration units C] | ≥3 | ≥4 | ≥5 | ≥6 | 7 ± 3 | 6 ± 2 | 6 ± 1 |
| fourth daily dose [μg] | 600 ± 20 | 600 ± 20 | 600 ± 20 | 600 ± 20 | 600 ± 20 | 600 ± 20 | 600 ± 20 |
| δ [number of administration units D] | ≥3 | ≥4 | ≥5 | ≥6 | 7 ± 3 | 6 ± 2 | 6 ± 1 |

| | $B_{22}$ | $B_{23}$ |
|---|---|---|
| first daily dose [μg] | 100 | 100 |
| α [days] | 6 | 7 |
| second daily dose [μg] | 200 | 200 |
| β [days] | 6 | 7 |
| third daily dose [μg] | 400 | 400 |
| γ [days] | 6 | 7 |
| fourth daily dose [μg] | 600 | 600 |
| δ [days] | ≥2 | ≥2 |

| | $C_1$ | $C_2$ | $C_3$ | $C_4$ | $C_5$ | $C_6$ | $C_7$ |
|---|---|---|---|---|---|---|---|
| first daily dose [μg] | 50 ± 40 | 50 ± 40 | 50 ± 40 | 50 ± 20 | 50 ± 20 | 50 ± 20 | 50 |
| α [number of administration units A] | ≥2 | ≥3 | 3 ± 1 | ≥2 | ≥3 | 3 ± 1 | 3 |
| second daily dose [μg] | 100 ± 80 | 100 ± 80 | 100 ± 80 | 100 ± 40 | 100 ± 40 | 100 ± 40 | 100 |
| β [number of administration units B] | ≥2 | ≥3 | 3 ± 1 | ≥2 | ≥3 | 3 ± 1 | 3 |
| third daily dose [μg] | 200 ± 80 | 200 ± 80 | 200 ± 80 | 200 ± 40 | 200 ± 40 | 200 ± 40 | 200 |
| γ [number of administration units C] | ≥2 | ≥3 | 3 ± 1 | ≥2 | ≥3 | 3 ± 1 | 3 |
| fourth daily dose [μg] | 300 ± 80 | 300 ± 80 | 300 ± 80 | 300 ± 40 | 300 ± 40 | 300 ± 40 | 300 |
| δ [number of administration units D] | ≥2 | ≥3 | 3 ± 1 | ≥2 | ≥3 | 3 ± 1 | 3 |
| fifth daily dose [μg] | 400 ± 80 | 400 ± 80 | 400 ± 80 | 400 ± 40 | 400 ± 40 | 400 ± 40 | 400 |
| ε [number of administration units E] | ≥2 | ≥3 | 3 ± 1 | ≥2 | ≥3 | 3 ± 1 | 3 |
| sixth daily dose [μg] | 500 ± 80 | 500 ± 80 | 500 ± 80 | 500 ± 40 | 500 ± 40 | 500 ± 40 | 500 |
| φ [number of administration units F] | ≥2 | ≥3 | 3 ± 1 | ≥2 | ≥3 | 3 ± 1 | 3 |
| seventh daily dose [μg] | 600 ± 80 | 600 ± 80 | 600 ± 80 | 600 ± 40 | 600 ± 40 | 600 ± 40 | 600 |
| χ [number of administration units G] | ≥2 | ≥3 | 3 ± 1 | ≥2 | ≥3 | 3 ± 1 | ≥2 |

The following examples describe the invention in greater detail and are intended to illustrate the invention but not to limit its scope.

Based upon pooled clinical data a dose-adverse-events-dropout model was developed. A logistic regression model was adopted to model the severity of adverse events. The predicted severity of adverse events was then incorporated into a time-to-dropout model as a covariate for the probability of dropout. The joint dose-adverse-event-dropout model was built to simultaneously model adverse events and dropout.

Model for severity of adverse event:

$$Logit[P(AE_{ij} \leq m)] = \sum_{k=0}^{m} \beta_k + f_p(t_j) + f_d(D_{ij}) + \eta_i$$

with
$AE_{ij}$=severity of adverse event (Nausea, Vomiting, Dizziness), i=subject, j=time
$P(AE_{ij} \leq m)$=probability that the severity of AE, $AE_{ij}$, for subject i at time j is ≤m, m∈[0,3)
$f_p(t_j)$ is the placebo/time effect at time j
$f_d(D_{ij})$ is Dose effect with $D_{ij}$=Dose for subject i at time j
$\beta_k$=population mean baseline Logit probability
$\eta_i$=inter-individual random effect
$Logit(p)=log(p/(1-p))$ Model for time to dropout:

$$h_{ij} = h_0 \times \exp(COV_{ij}) \quad COV_{ij} = \theta_{PAE} \times PAE_{ij}$$

$$S_{ij} = \exp\left(-\int_0^j h_{ij}\right) \quad f_{ij} = S_{ij} \times h_{ij}$$

with
$h_{ij}$ is the hazard for subject i at time j, which described as the instantaneous probability of dropout at the short period after j, given that the subject has not dropout up to time j
$h_0$ is the hazard without influence of covariate (COV)
$PAE_{ij}$: Predicted severity of AE from the logit model, for subject i at time j
$\theta_{PAE}$ is the influence of severity of AE on the hazard
$S_{ij}$ is the likelihood of no dropout for subject i at time j
$f_{ij}$ is the probability density of dropout for subject i at time j References: Kowalski et al, 2003(30), 315-336, JPKPD; Frame et al, 2009(36), 565-584, JPKPD Models from these references were adapted to construct the current joint Dose-AE-Dropout model.

A population pharmacokinetic-pharmacodynamic model was developed to estimate the effect of several doses of Cebranopadol in a Low Back pain population. The results are shown in FIG. 1.

Based on this model, FIG. 1 shows the dependency of the placebo corrected Cebranopadol effect from the concentrations corresponding to the administered doses. The vertical lines indicate the margins for the plasma concentrations of Cebranopadol after oral administration of 200 μg, 400 μg and 600 μg, respectively. The plasma concentrations are predicted as median concentrations (90% confidence interval) at the end of the trial, assuming perfect compliance and no dropout. The horizontal line indicates a clinically significant threshold for the placebo corrected Cebranopadol effect of 0.7.

Figure 2:
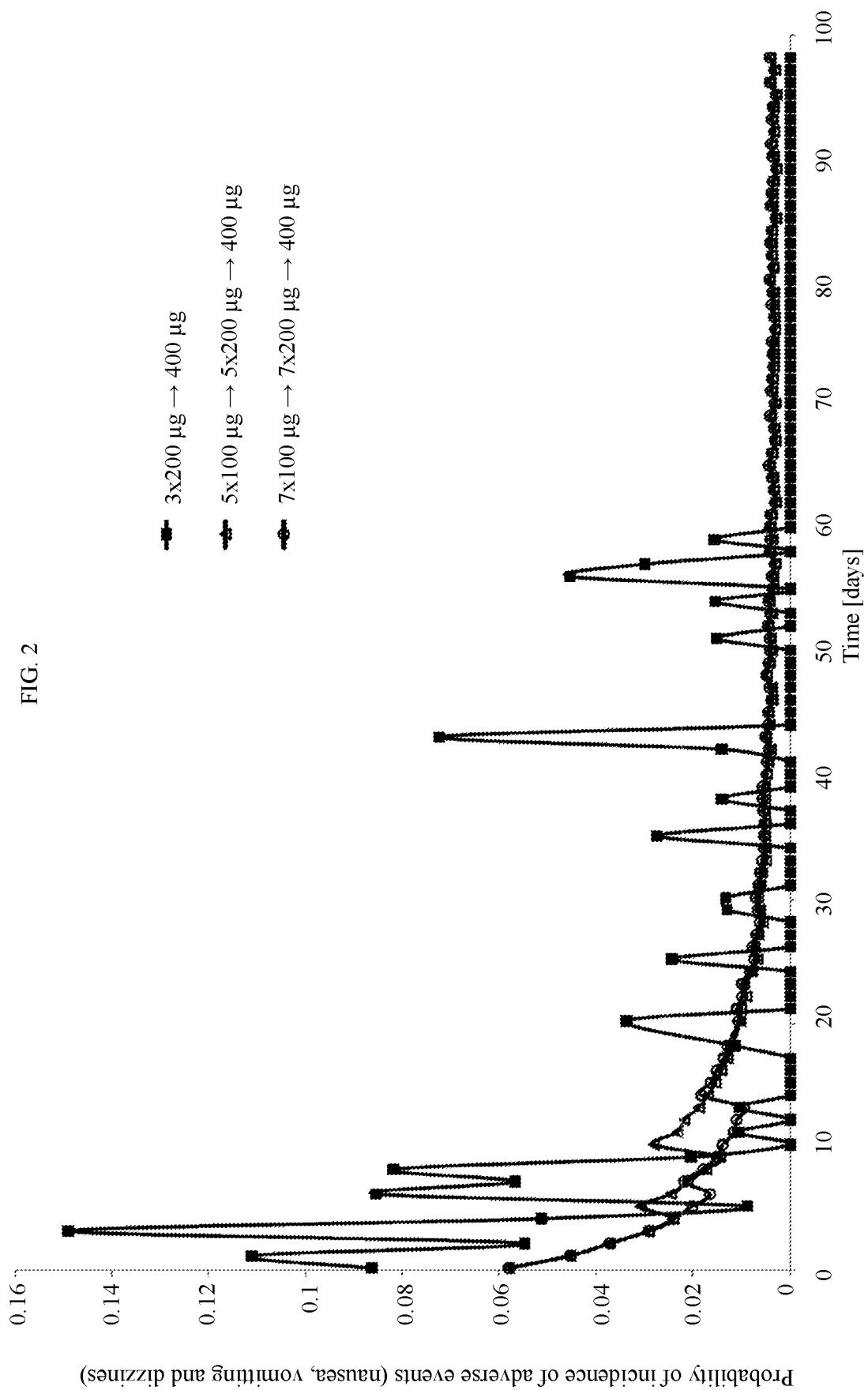
Figure 3:
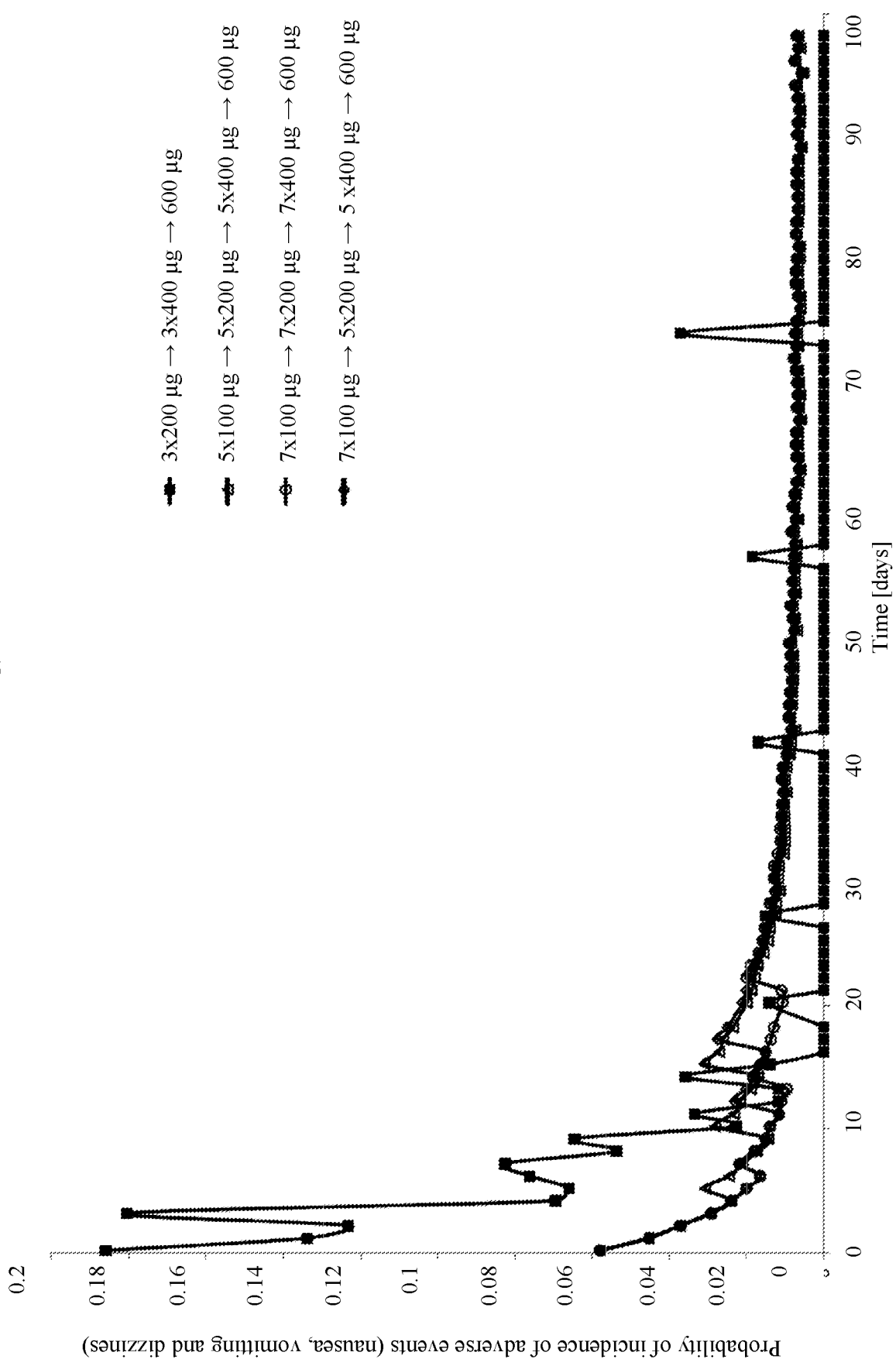

FIGS. 2 and 3 show the probability of the adverse events nausea, vomiting and dizziness.

FIG. 2 shows the incidence of nausea, vomiting and dizziness as observed in a clinical trial where treatment was initiated with a daily dose of 200 μg which after 3 days was increased to a daily dose of 400 μg (■).

These observed adverse events are compared with the simulated results for two different titration regimens also reaching a final dose of 400 μg of Cebranopadol.

According to one titration regimen (Δ), a first daily dose of 100 μg of Cebranopadol is administered once daily during a first administration interval of 5 days, a second daily dose of 200 μg of Cebranopadol is administered once daily during a second administration interval of 5 days, and a constant third daily dose of 400 μg of Cebranopadol is administered once daily thereafter.

According to another titration regimen (○), a first daily dose of 100 μg of Cebranopadol is administered once daily during a first administration interval of 7 days, a second daily dose of 200 μg of Cebranopadol is administered once daily during a second administration interval of 7 days, and a constant third daily dose of 400 μg of Cebranopadol is administered once daily thereafter.

It becomes clear from these simulations that both titration regimens significantly reduce the probability of incidence of the adverse events nausea, vomiting and dizziness and hence will reduce the number of dropouts due to these adverse events.

FIG. 3 shows the incidence of nausea, vomiting and dizziness as observed in a clinical trial where treatment was initiated with a daily dose of 200 μg which after 3 days was increased to a daily dose of 400 μg and subsequently to a final daily dose of 600 μg (■).

These observed adverse events are compared with the calculated results for 3 different titration regimes also reaching a final dose of 600 μg of Cebranopadol.

According to one titration regimen (Δ), a first daily dose of 100 μg of Cebranopadol is administered once daily during a first administration interval of 5 days, a second daily dose of 200 μg of Cebranopadol is administered once daily during a second administration interval of 5 days, a third daily dose of 400 μg of Cebranopadol is administered once daily during a third administration interval of 5 days, and a constant third daily dose of 600 μg of Cebranopadol is administered once daily thereafter.

According to another titration regimen (○), a first daily dose of 100 μg of Cebranopadol is administered once daily during a first administration interval of 7 days, a second daily dose of 200 μg of Cebranopadol is administered once daily during a second administration interval of 7 days, a third daily dose of 400 μg of Cebranopadol is administered once daily during a third administration interval of 7 days, and a constant third daily dose of 600 μg of Cebranopadol is administered once daily thereafter.

According to still another titration regime (◇), a first daily dose of 100 μg of Cebranopadol is administered once daily during a first administration interval of 7 days, a second daily dose of 200 μg of Cebranopadol is administered once daily during a second administration interval of 5 days, a third daily dose of 400 μg of Cebranopadol is administered once daily during a third administration interval of 5 days, and a constant third daily dose of 600 μg of Cebranopadol is administered once daily thereafter.

It becomes clear from these simulations that all three titration regimens significantly reduce the probability of incidence of adverse events nausea, vomiting and dizziness and hence will reduce the number of dropouts due to these adverse events.

Figure 4:
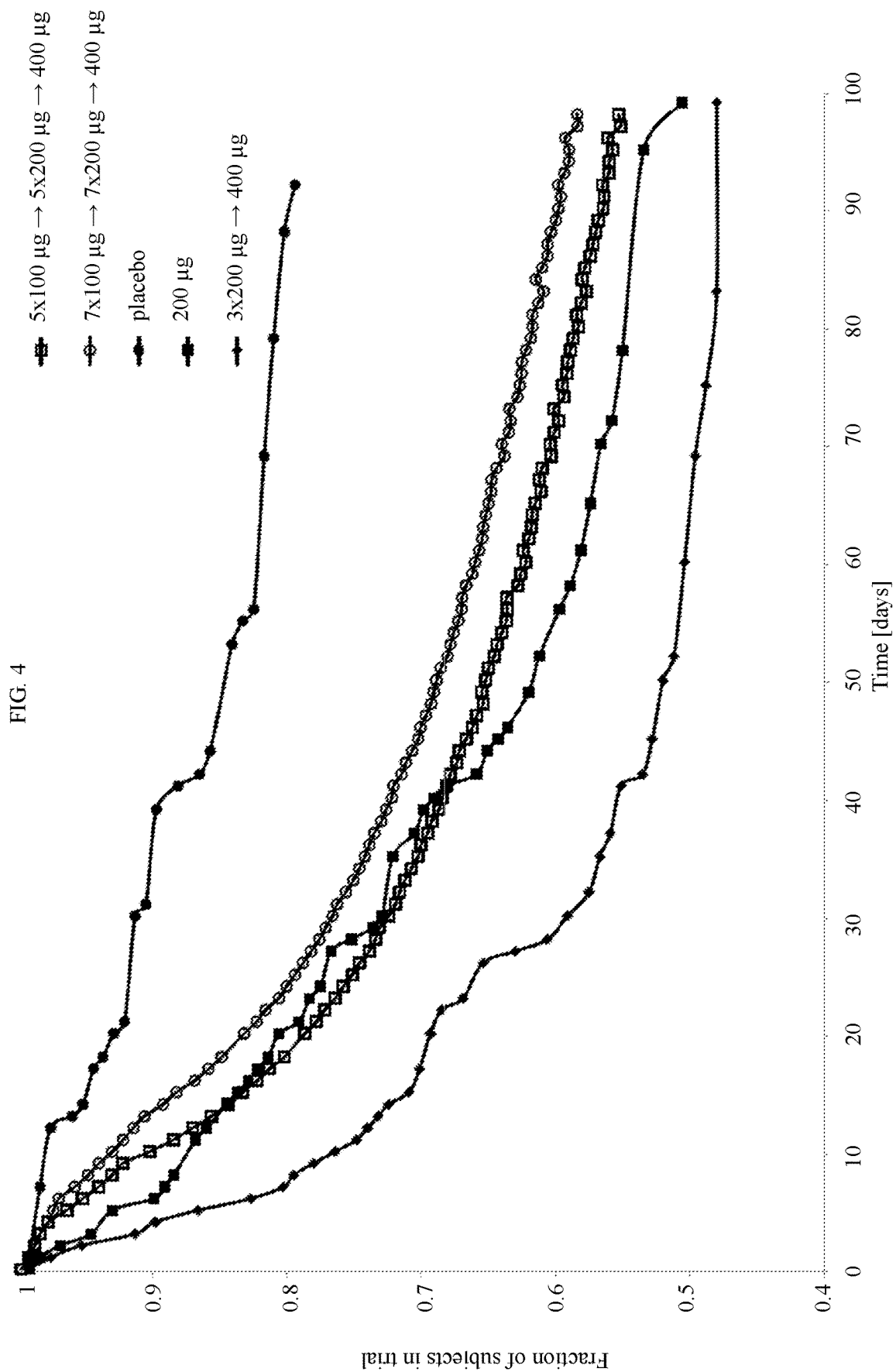
Figure 5:
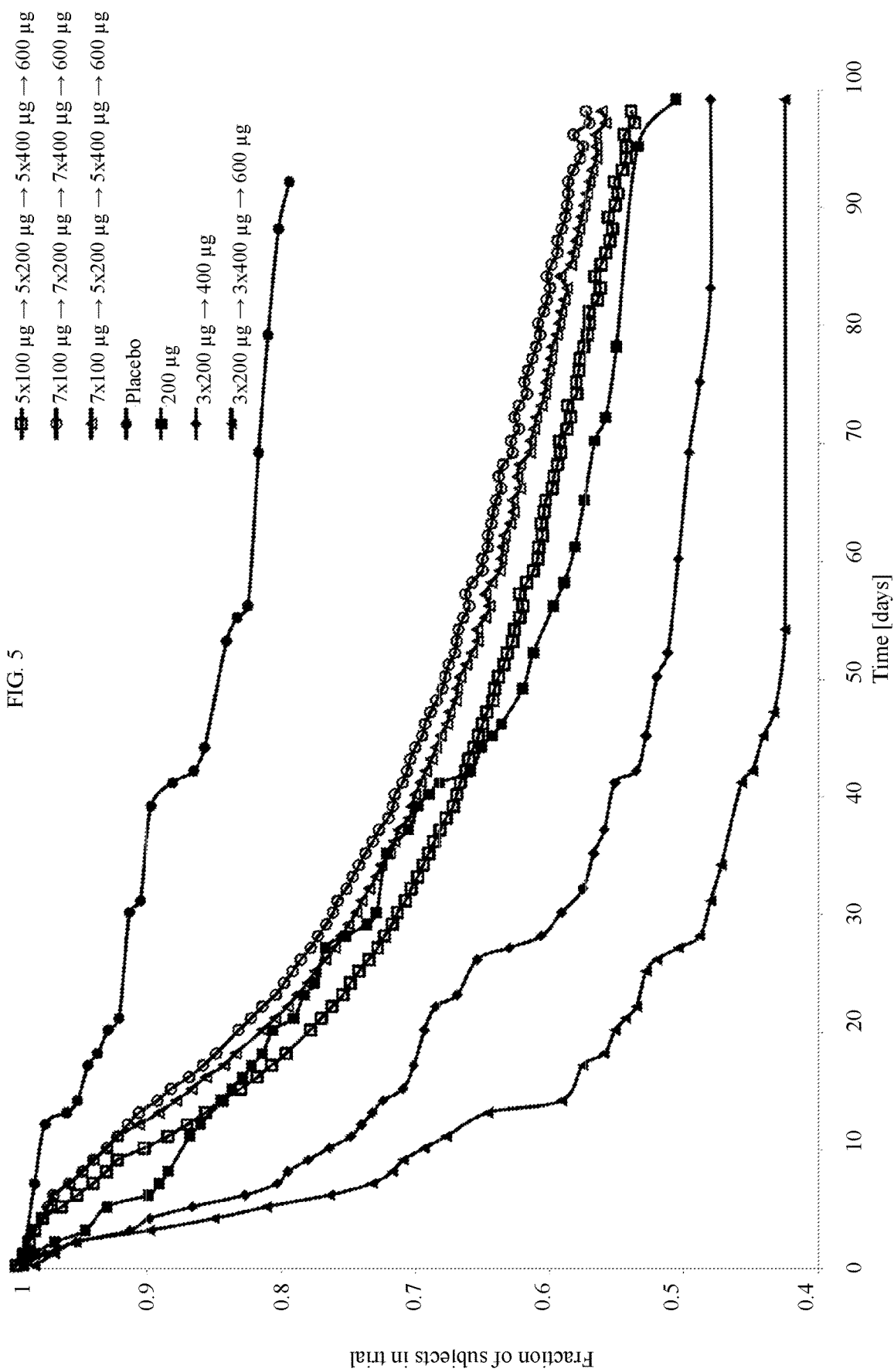

FIGS. 4 and 5 show the simulated total dropout corresponding to the simulated adverse event profiles previously displayed in FIGS. 2 and 3.

FIG. 4 shows the total dropouts for placebo (●), 200 μg of Cebranopadol (■) or 400 μg of Cebranopadol (♦) in each case administered once daily (400 μg of Cebranopadol was administered on day 4 after 3 days 200 μg of Cebranopadol).

These total dropouts are compared with the simulated results for two different titration regimens reaching a final dose of 400 μg of Cebranopadol corresponding to the simulated adverse event profiles displayed in FIG. 2.

According to one titration regime (□), a first daily dose of 100 μg of Cebranopadol is administered once daily during a first administration interval of 5 days, a second daily dose of 200 μg of Cebranopadol is administered once daily during a second administration interval of 5 days, and a constant third daily dose of 400 μg of Cebranopadol is administered once daily thereafter.

According to another titration regime (○), a first daily dose of 100 μg of Cebranopadol is administered once daily during a first administration interval of 7 days, a second daily dose of 200 μg of Cebranopadol is administered once daily during a second administration interval of 7 days, and a constant third daily dose of 400 μg of Cebranopadol is administered once daily thereafter.

It becomes clear from these simulations that both titration regimens significantly reduce the number of total dropouts.

FIG. 5 shows the total dropouts for placebo (●), 200 μg of Cebranopadol (■), 400 μg of Cebranopadol (♦), or 600 μg of Cebranopadol (▲) in each case administered once daily (400 μg of Cebranopadol was administered on day 4 after 3 days 200 μg of Cebranopadol; 600 μg of Cebranopadol was administered on day 7 after 3 days 200 μg of Cebranopadol followed by 3 days 400 μg of Cebranopadol).

These total dropouts are compared with the simulated results for three different titration regimens reaching a final dose of 600 μg of Cebranopadol.

According to one titration regime (□), a first daily dose of 100 μg of Cebranopadol is administered once daily during a first administration interval of 5 days, a second daily dose of 200 μg of Cebranopadol is administered once daily during a second administration interval of 5 days, a third daily dose of 400 μg of Cebranopadol is administered once daily during a third administration interval of 5 days, and a constant third daily dose of 600 μg of Cebranopadol is administered once daily thereafter.

According to another titration regime (○), a first daily dose of 100 μg of Cebranopadol is administered once daily during a first administration interval of 7 days, a second daily dose of 200 μg of Cebranopadol is administered once daily during a second administration interval of 7 days, a third daily dose of 400 µg of Cebranopadol is administered once daily during a third administration interval of 7 days, and a constant third daily dose of 600 µg of Cebranopadol is administered once daily thereafter.

According to still another titration regime (Δ), a first daily dose of 100 µg of Cebranopadol is administered once daily during a first administration interval of 7 days, a second daily dose of 200 µg of Cebranopadol is administered once daily during a second administration interval of 5 days, a third daily dose of 400 µg of Cebranopadol is administered once daily during a third administration interval of 5 days, and a constant third daily dose of 600 µg of Cebranopadol is administered once daily thereafter.

It becomes clear from these simulations that all three titration regimens significantly reduce the number of total dropouts.

Figure 6:
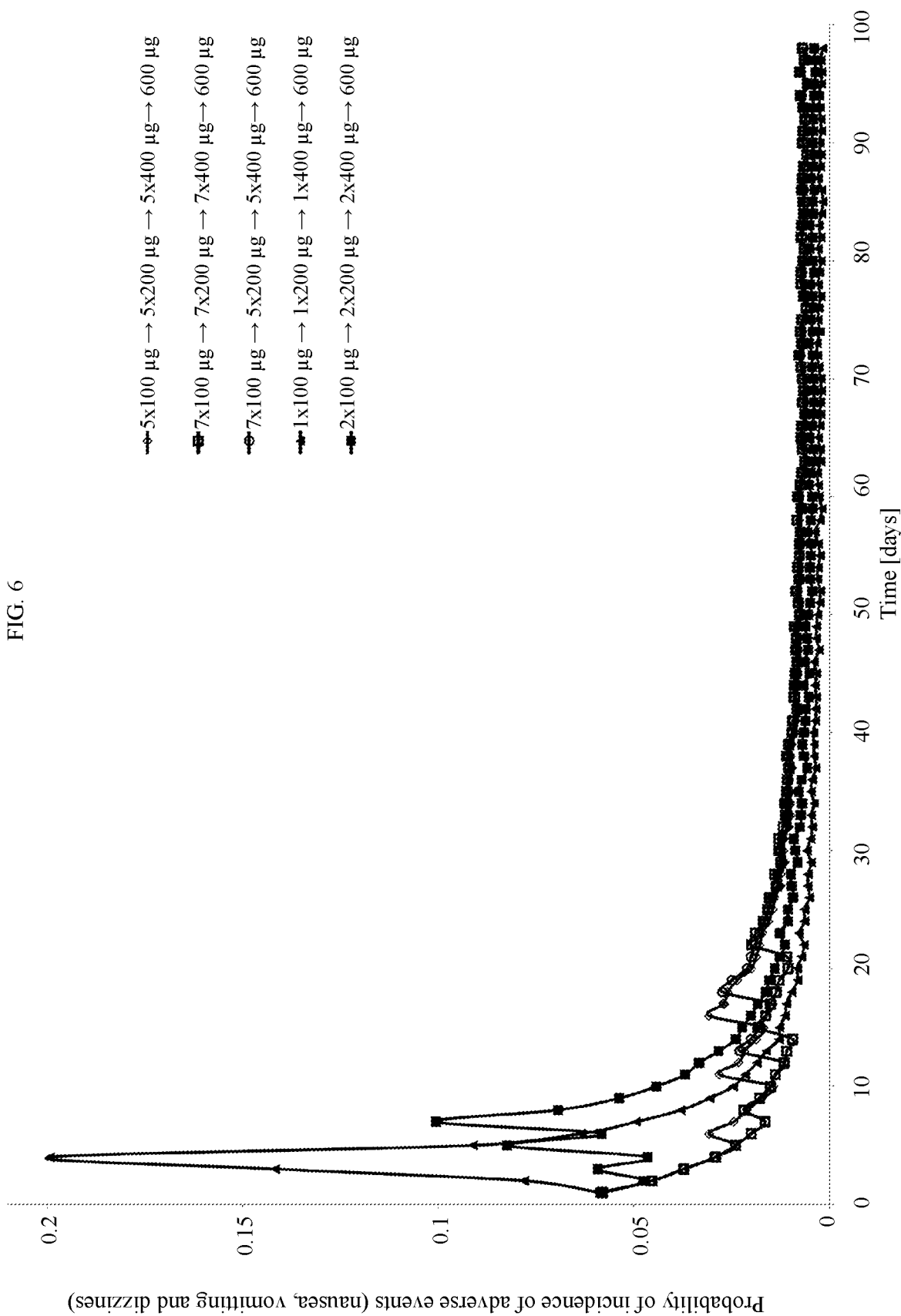

FIG. 6 shows the probability of adverse events nausea, vomiting or dizziness as a function of days. The simulated results for different administration regimens each reaching a final daily dose of 600 µg of Cebranopadol through the same intermediate doses (100 µg, 200 µg, and 400 µg) are compared with one another. According to the fastest titration regimen (▲), the daily dose of Cebranopadol is increased every day. According to the second fastest titration regimen (■), the daily dose of Cebranopadol is increased every second day. According to the other three titration regimens (◇, ○, □), the daily dose of Cebranopadol is increased after administration intervals lasting for five and seven days, respectively.

Figure 7:
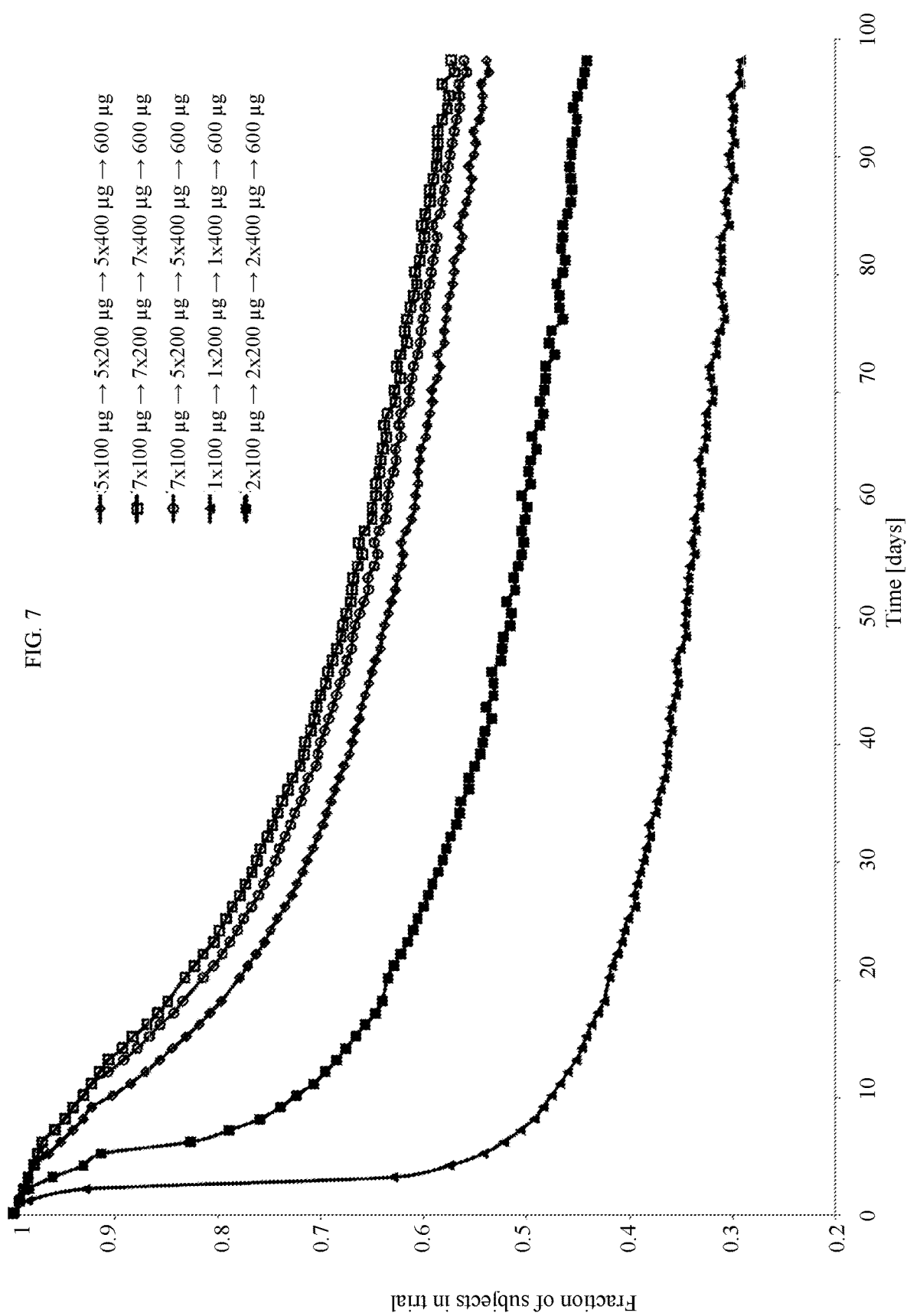

FIG. 7 shows the total dropout by different doses. The simulated results for different administration regimens each reaching a final daily dose of 600 µg of Cebranopadol through the same intermediate doses (100 µg, 200 µg, and 400 µg) are compared with one another. According to the fastest titration regimen (▲), the daily dose of Cebranopadol is increased every day. According to the second fastest titration regimen (■), the daily dose of Cebranopadol is increased every second day. According to the other three titration regimens (◇, ○, □), the daily dose of Cebranopadol is increased after administration intervals lasting for five and seven days, respectively.

It becomes clear from these simulations that the slower titration regimens significantly reduce the probability of the incidence of adverse events (nausea, vomiting, dizziness) and the number of total dropouts, respectively.

Figure 8:
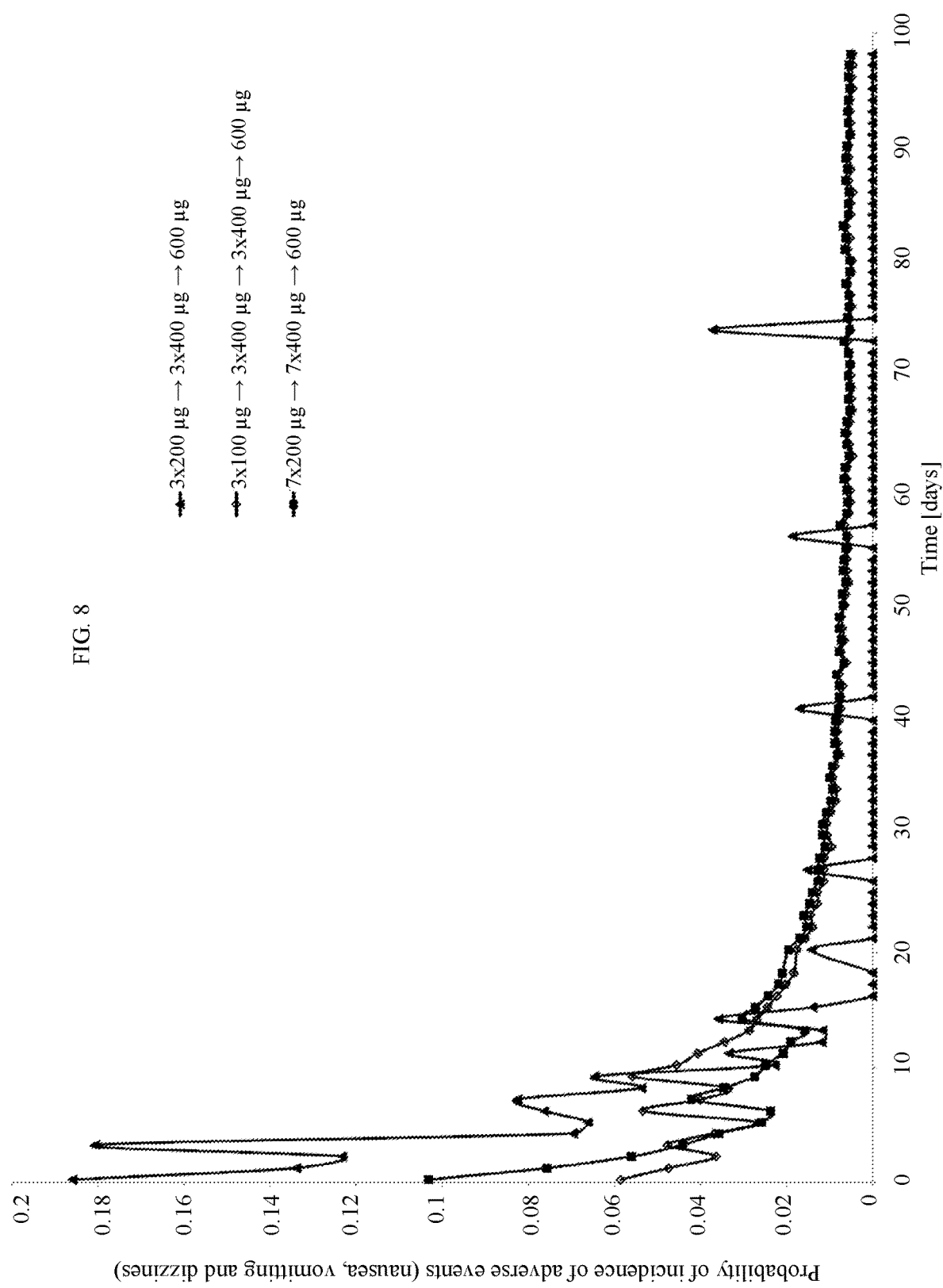
FIG. 8 shows the probability of adverse events nausea, vomiting or dizziness as a function of days. The simulated results for different administration regimens each reaching a final daily dose of 600 µg of Cebranopadol are compared with one another and with a clinical trial where treatment was initiated with a daily dose of 200 µg which was later increased to a daily dose of 400 µg and subsequently to a final daily dose of 600 µg.

FIG. 8 shows the probability of adverse events nausea, vomiting or dizziness as a function of days. The simulated results for two different administration regimens each reaching a final daily dose of 600 µg of Cebranopadol (◇, ■) are compared with one another and with a clinical trial where treatment was initiated with a daily dose of 200 µg which was later increased to a daily dose of 400 µg and subsequently to a final daily dose of 600 µg (▲).

Figure 9:
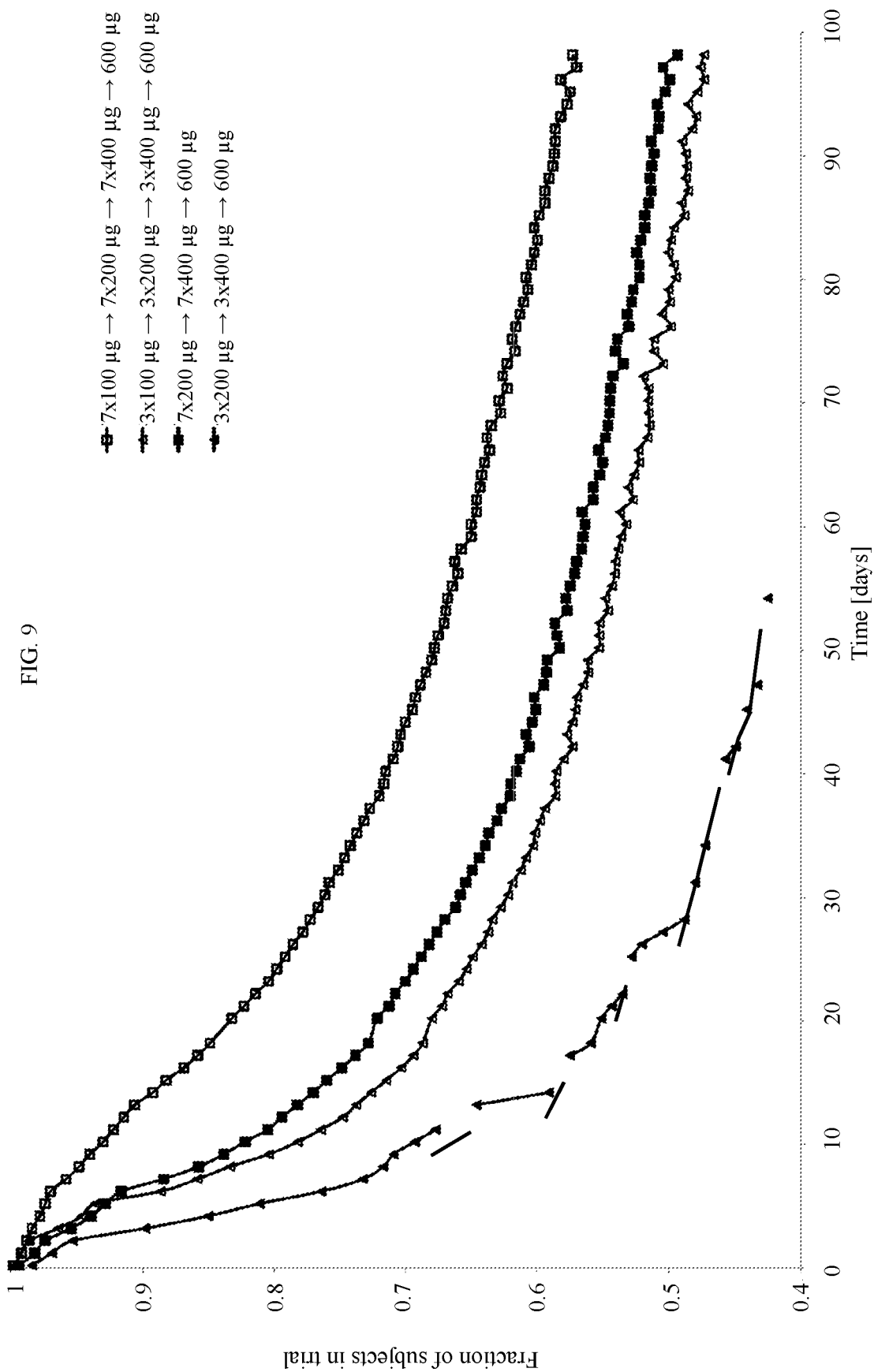
FIG. 9 shows the total dropout by different doses. The simulated results for different administration regimens each reaching a final daily dose of 600 µg of Cebranopadol are compared with one another and with a clinical trial where treatment was initiated with a daily dose of 200 µg which was later increased to a daily dose of 400 µg and subsequently to a final daily dose of 600 µg.

FIG. 9 shows the total dropout by different dosing schemes. The simulated results for three different administration regimens each reaching a final daily dose of 600 µg of Cebranopadol (□, Δ, ■) are compared with one another and with a clinical trial where treatment was initiated with a daily dose of 200 µg which was later increased to a daily dose of 400 µg and subsequently to a final daily dose of 600 µg (▲).

It becomes clear from these simulations that by adjusting the first daily dose of Cebranopadol as well as the length of the administration intervals, the probability of the incidence of adverse events (nausea, vomiting, dizziness) and the number of total dropouts, respectively, can be significantly reduced. Satisfactory results are achieved when the first daily dose is sufficiently low and the administration intervals are sufficiently long.

Figure 10:
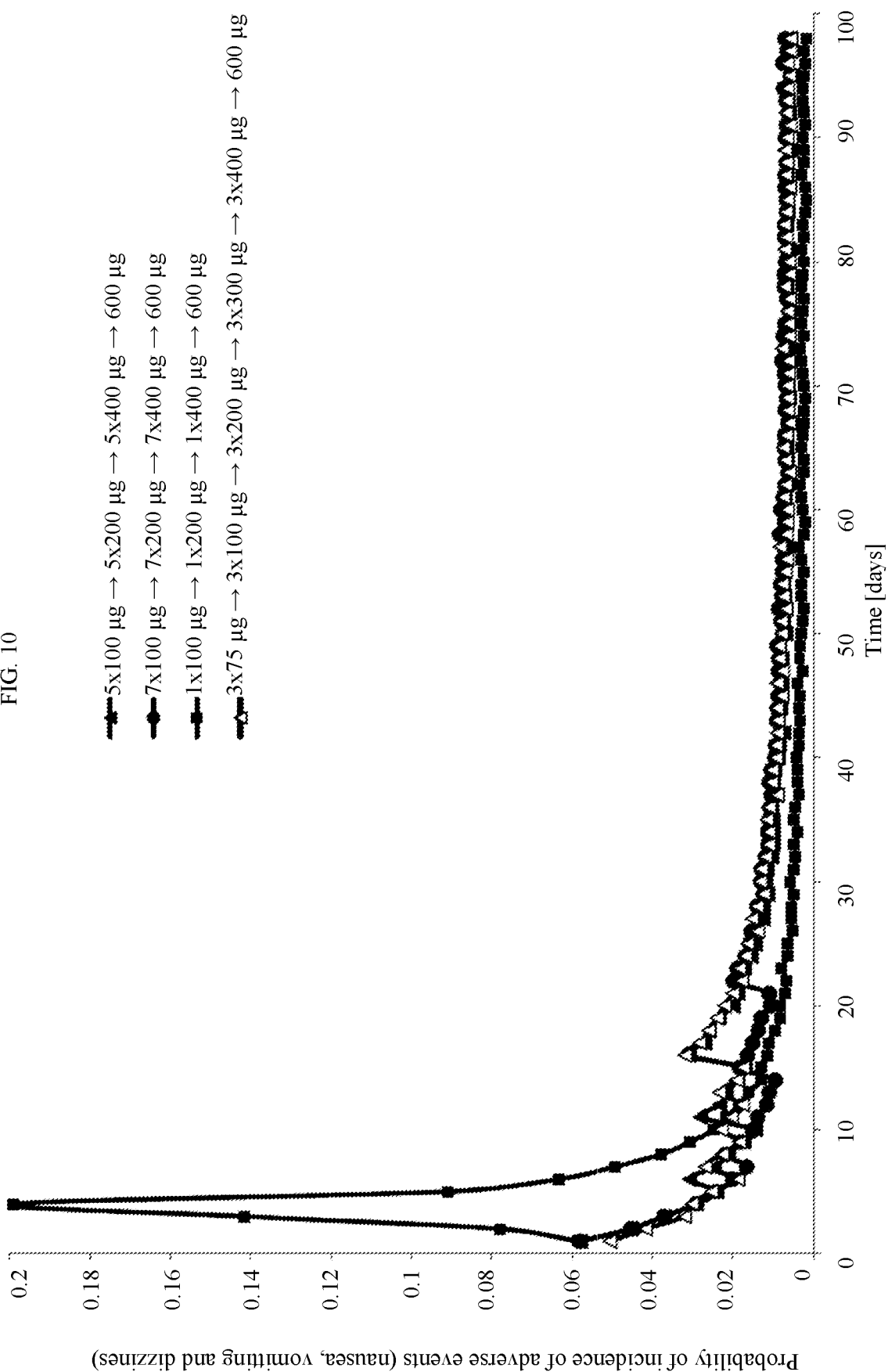
FIG. 10 shows the probability of adverse events nausea, vomiting or dizziness as a function of days. The simulated results for different administration regimens each reaching a final daily dose of 600 µg of Cebranopadol are compared with one another including an administration regimen beginning at an initial daily dose of 75 µg.
Figure 11:
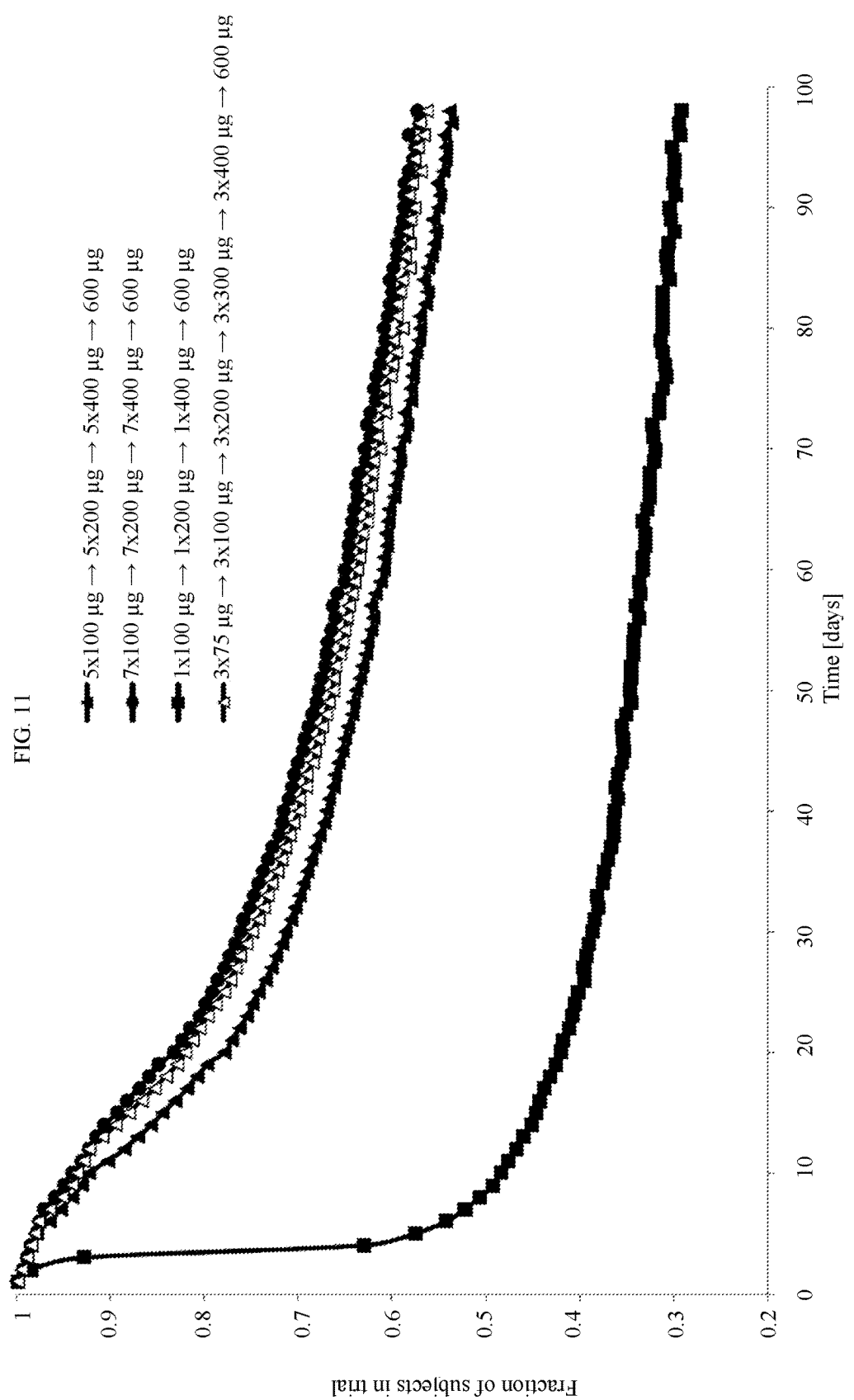
FIG. 11 shows the total dropout by different doses. The simulated results for different administration regimens each reaching a final daily dose of 600 µg of Cebranopadol are compared with one another including an administration regimen beginning at an initial daily dose of 75 µg.

FIGS. 10 and 11 are related to FIGS. 8 and 9, respectively, but additionally include an administration regimen beginning at an initial daily dose of 75 µg.

The invention claimed is:

1. A method of treating pain in a patient in need of such treatment, said method comprising administering Cebranopadol according to an administration regimen comprising:
   (i) a first administration interval, which lasts for at least 2 consecutive days, wherein a first daily dose of Cebranopadol is administered on every day of the first administration interval, wherein the first daily dose of Cebranopadol is in an amount that is expected to be subtherapeutic for the patient;
   (ii) a second administration interval, which lasts for at least 2 consecutive days and directly follows the first administration interval without interruption, wherein a second daily dose of Cebranopadol is administered on every day of the second administration interval; and
   (iii) a third administration interval, which lasts for at least 2 consecutive days and directly follows the second administration interval without interruption, wherein a third daily dose of Cebranopadol is administered on every day of the third administration interval;
   wherein the first daily dose of Cebranopadol is lower than the second daily dose of Cebranopadol; and
   wherein the second daily dose of Cebranopadol is lower than the third daily dose of Cebranopadol.

2. The method according to claim 1, wherein
   the first daily dose of Cebranopadol is less than 200 µg; and/or
   the first administration interval lasts for at least 4 consecutive days.

3. The method according to claim 1, wherein the first daily dose of Cebranopadol is within the range of from 30 to 70 wt.-% of the second daily dose of Cebranopadol.

4. The method according to claim 1, wherein
   the first daily dose of Cebranopadol is within the range of from 10 to 190 µg; and/or
   the second daily dose of Cebranopadol is within the range of from 110 to 290 µg.

5. The method according to claim 1, wherein the first daily dose of Cebranopadol is within the range of from 5 to 45 wt.-% of the third daily dose of Cebranopadol and wherein the second daily dose of Cebranopadol is within the range of from 30 to 70 wt.-% of the third daily dose of Cebranopadol.

6. The method according to claim 1, wherein the third daily dose of Cebranopadol is within the range of from 310 to 490 µg.

7. The method according to claim 1, wherein the administration regimen additionally comprises
   (iv) a fourth administration interval, which lasts for at least 2 consecutive days and directly follows the third administration interval without interruption, wherein a fourth daily dose of Cebranopadol is administered on every day of the fourth administration interval;
   wherein the third daily dose of Cebranopadol is lower than the fourth daily dose of Cebranopadol.

8. The method according to claim 7, wherein the first daily dose of Cebranopadol is within the range of from 5 to 30 wt.-% of the fourth daily dose of Cebranopadol, wherein the second daily dose of Cebranopadol is within the range of from 15 to 50 wt.-% of the fourth daily dose of Cebranopadol, and wherein the third daily dose of Cebranopadol is within the range of from 50 to 75 wt.-% of the fourth daily dose of Cebranopadol.

9. The method according to claim 7, wherein the fourth daily dose of Cebranopadol is within the range of from 510 to 690 μg.

10. The method according to claim 1, wherein the first daily dose of Cebranopadol, the second daily dose of Cebranopadol, the third daily dose of Cebranopadol, and/or an optional fourth daily dose of Cebranopadol independently of one another are administered orally.

11. The method according to claim 1, wherein the first daily dose of Cebranopadol, the second daily dose of Cebranopadol, the third daily dose of Cebranopadol, and/or an optional fourth daily dose of Cebranopadol independently of one another are administered once daily (sid).

12. The method according to claim 1, wherein
   (i) the first administration interval, the second administration interval, the third administration interval, and/or an optional fourth administration interval, and/or an optional fifth administration interval, and/or an optional sixth administration interval, and/or an optional seventh administration interval independently of one another last for 5 to 7 consecutive days; or
   (ii) the first administration interval, the second administration interval, the third administration interval, and/or an optional fourth administration interval, and/or an optional fifth administration interval, and/or an optional sixth administration interval, and/or an optional seventh administration interval independently of one another last for 2 to 4 consecutive days.

13. The method according to claim 1, wherein the administration regimen comprises
   (i) a first administration interval, which lasts for at least $\alpha$ consecutive days, wherein a first daily dose of Cebranopadol is orally administered on every day of the first administration interval;
   (ii) a second administration interval, which lasts for at least $\beta$ consecutive days and directly follows the first administration interval without interruption, wherein a second daily dose of Cebranopadol is orally administered on every day of the second administration interval;
   (iii) a third administration interval, which lasts for at least $\gamma$ consecutive days and directly follows the second administration interval without interruption, wherein a third daily dose of Cebranopadol is orally administered on every day of the third administration interval; and
   (iv) optionally, a fourth administration interval, which lasts for at least $\delta$ consecutive days and directly follows the third administration interval without interruption, wherein a fourth daily dose of Cebranopadol is orally administered on every day of the fourth administration interval;
   (v) optionally, a fifth administration interval, which lasts for at least $\varepsilon$ consecutive days and directly follows the fourth administration interval without interruption, wherein a fifth daily dose of Cebranopadol is orally administered on every day of the fifth administration interval; and
   (vi) optionally, a sixth administration interval, which lasts for at least $\varphi$ consecutive days and directly follows the fifth administration interval without interruption, wherein a sixth daily dose of Cebranopadol is orally administered on every day of the sixth administration interval; and
   (vii) optionally, a seventh administration interval, which lasts for at least $\chi$ consecutive days and directly follows the sixth administration interval without interruption, wherein a seventh daily dose of Cebranopadol is orally administered on every day of the seventh administration interval;

and satisfies any of the following requirements $A_1$ to $C_3$:

|  | $A_1$ | $A_2$ | $A_{10}$ | $A_{12}$ | $A_{20}$ | $A_{21}$ |
|---|---|---|---|---|---|---|
| first daily dose [μg] | 100 ± 80 | 100 ± 80 | 100 ± 50 | 100 ± 50 | 100 ± 20 | 100 ± 20 |
| $\alpha$ [days] | ≥3 | ≥4 | ≥5 | 7 ± 3 | 6 ± 2 | 6 ± 1 |
| second daily dose [μg] | 200 ± 80 | 200 ± 80 | 200 ± 50 | 200 ± 50 | 200 ± 20 | 200 ± 20 |
| $\beta$ [days] | ≥3 | ≥4 | ≥5 | 7 ± 3 | 6 ± 2 | 6 ± 1 |
| third daily dose [μg] | 400 ± 80 | 400 ± 80 | 400 ± 50 | 400 ± 50 | 400 ± 20 | 400 ± 20 |
| $\gamma$ [days] | ≥3 | ≥4 | ≥5 | 7 ± 3 | 6 ± 2 | 6 ± 1 |

|  | $B_1$ | $B_2$ | $B_{10}$ | $B_{12}$ | $B_{20}$ | $B_{21}$ |
|---|---|---|---|---|---|---|
| first daily dose [μg] | 100 ± 80 | 100 ± 80 | 100 ± 50 | 100 ± 50 | 100 ± 20 | 100 ± 20 |
| $\alpha$ [days] | ≥3 | ≥4 | ≥5 | 7 ± 3 | 6 ± 2 | 6 ± 1 |
| second daily dose [μg] | 200 ± 80 | 200 ± 80 | 200 ± 50 | 200 ± 50 | 200 ± 20 | 200 ± 20 |
| $\beta$ [days] | ≥3 | ≥4 | ≥5 | 7 ± 3 | 6 ± 2 | 6 ± 1 |
| third daily dose [μg] | 400 ± 80 | 400 ± 80 | 400 ± 50 | 400 ± 50 | 400 ± 20 | 400 ± 20 |
| $\gamma$ [days] | ≥3 | ≥4 | ≥5 | 7 ± 3 | 6 ± 2 | 6 ± 1 |
| fourth daily dose [μg] | 600 ± 80 | 600 ± 80 | 600 ± 50 | 600 ± 50 | 600 ± 20 | 600 ± 20 |
| $\delta$ [days] | ≥3 | ≥4 | ≥5 | 7 ± 3 | 6 ± 2 | 6 ± 1 |

|  | $C_1$ | $C_2$ | $C_3$ |
|---|---|---|---|
| first daily dose [µg] | 50 ± 40 | 50 ± 40 | 50 ± 40 |
| α [days] | ≥2 | ≥3 | 3 ± 1 |
| second daily dose [µg] | 100 ± 80 | 100 ± 80 | 100 ± 80 |
| β [days] | ≥2 | ≥3 | 3 ± 1 |
| third daily dose [µg] | 200 ± 80 | 200 ± 80 | 200 ± 80 |
| γ [days] | ≥2 | ≥3 | 3 ± 1 |
| fourth daily dose [µg] | 300 ± 80 | 300 ± 80 | 300 ± 80 |
| δ [days] | ≥2 | ≥3 | 3 ± 1 |
| fifth daily dose [µg] | 400 ± 80 | 400 ± 80 | 400 ± 80 |
| ε [days] | ≥2 | ≥3 | 3 ± 1 |
| sixth daily dose [µg] | 500 ± 80 | 500 ± 80 | 500 ± 80 |
| φ [days] | ≥2 | ≥3 | 3 ± 1 |
| seventh daily dose [µg] | 600 ± 80 | 600 ± 80 | 600 ± 80 |
| χ [days] | ≥2 | ≥3 | 3 ± 1 |

14. The method according to claim 1, wherein the pain is acute pain or chronic pain; and/or
nociceptive pain or neuropathic pain; and/or
postoperative pain, malignant pain, and/or inflammatory pain.

15. A method of reducing side effects associated with treatment for pain, said method comprising administering Cebranopadol according to an administration regimen comprising:
(i) a first administration interval, which lasts for at least 2 consecutive days, wherein a first daily dose of Cebranopadol is administered on every day of the first administration interval, wherein the first daily dose of Cebranopadol is in an amount that is expected to be subtherapeutic for the patient;
(ii) a second administration interval, which lasts for at least 2 consecutive days and directly follows the first administration interval without interruption, wherein a second daily dose of Cebranopadol is administered on every day of the second administration interval; and
(iii) an optional third administration interval, which lasts for at least 2 consecutive days and directly follows the second administration interval without interruption, wherein a third daily dose of Cebranopadol is administered on every day of the third administration interval;
wherein the first daily dose of Cebranopadol is lower than the second daily dose of Cebranopadol; and
wherein the second daily dose of Cebranopadol is lower than the optional third daily dose of Cebranopadol.

16. The method according to claim 15, wherein
the first daily dose of Cebranopadol is less than 200 µg; and/or
the first administration interval lasts for at least 4 consecutive days.

17. The method according to claim 15, wherein the first daily dose of Cebranopadol is within the range of from 30 to 70 wt.-% of the second daily dose of Cebranopadol.

18. The method according to claim 15, wherein
the first daily dose of Cebranopadol is within the range of from 60 to 140 µg; and/or
the second daily dose of Cebranopadol is within the range of from 160 to 240 µg.

19. The method according to claim 15, wherein the first daily dose of Cebranopadol is within the range of from 5 to 45 wt.-% of the third daily dose of Cebranopadol and wherein the second daily dose of Cebranopadol is within the range of from 30 to 70 wt.-% of the third daily dose of Cebranopadol.

20. The method according to claim 15, wherein the third daily dose of Cebranopadol is 95-105 µg greater than the second daily dose of Cebranopadol.

21. The method according to claim 15, wherein the administration regimen additionally comprises
(iv) a fourth administration interval, which lasts for at least 2 consecutive days and directly follows the third administration interval without interruption, wherein a fourth daily dose of Cebranopadol is administered on every day of the fourth administration interval;
wherein the third daily dose of Cebranopadol is lower than the fourth daily dose of Cebranopadol.

22. The method according to claim 21, wherein the first daily dose of Cebranopadol is within the range of from 5 to 30 wt.-% of the fourth daily dose of Cebranopadol, wherein the second daily dose of Cebranopadol is within the range of from 15 to 50 wt.-% of the fourth daily dose of Cebranopadol, and wherein the third daily dose of Cebranopadol is within the range of from 55 to 80 wt.-% of fourth daily dose of Cebranopadol.

23. The method according to claim 21, wherein the fourth daily dose of Cebranopadol is 95-105 µg greater than the third daily dose of Cebranopadol.

24. The method according to claim 21, wherein the first daily dose of Cebranopadol, the second daily dose of Cebranopadol, the third daily dose of Cebranopadol, and/or the fourth daily dose of Cebranopadol independently of one another are administered orally.

25. The method according to claim 21, wherein the first daily dose of Cebranopadol, the second daily dose of Cebranopadol, the third daily dose of Cebranopadol, and/or the fourth daily dose of Cebranopadol independently of one another are administered once daily (sid).

26. The method according to claim 15, wherein
(i) the first administration interval, the second administration interval, the optional third administration interval, and/or an optional fourth administration interval, and/or an optional fifth administration interval, and/or an optional sixth administration interval, and/or an optional seventh administration interval independently of one another last for 5 to 7 consecutive days; or
(ii) the first administration interval, the second administration interval, and/or an optional third administration interval, and/or an optional fourth administration interval, and/or an optional fifth administration interval, and/or an optional sixth administration interval, and/or an optional seventh administration interval independently of one another last for 2 to 4 consecutive days.

27. The method according to claim 15, wherein the administration regimen comprises
(i) a first administration interval, which lasts for at least α consecutive days, wherein a first daily dose of Cebranopadol is orally administered on every day of the first administration interval; and
(ii) a second administration interval, which lasts for at least β consecutive days and directly follows the first administration interval without interruption, wherein a second daily dose of Cebranopadol is orally administered on every day of the second administration interval;
and satisfies any of the following requirements $A_1$ to $C_3$:

|  | $A_1$ | $A_2$ | $A_{10}$ | $A_{12}$ | $A_{20}$ | $A_{21}$ |
|---|---|---|---|---|---|---|
| first daily dose [µg] | 100 ± 80 | 100 ± 80 | 100 ± 50 | 100 ± 50 | 100 ± 20 | 100 ± 20 |
| α [days] | ≥3 | ≥4 | ≥5 | 7 ± 3 | 6 ± 2 | 6 ± 1 |

-continued

|  | $A_1$ | $A_2$ | $A_{10}$ | $A_{12}$ | $A_{20}$ | $A_{21}$ |
|---|---|---|---|---|---|---|
| second daily dose [µg] | 200 ± 80 | 200 ± 80 | 200 ± 50 | 200 ± 50 | 200 ± 20 | 200 ± 20 |
| β [days] | ≥3 | ≥4 | ≥5 | 7 ± 3 | 6 ± 2 | 6 ± 1 |

|  | $B_1$ | $B_2$ | $B_{10}$ | $B_{12}$ | $B_{20}$ | $B_{21}$ |
|---|---|---|---|---|---|---|
| first daily dose [µg] | 100 ± 80 | 100 ± 80 | 100 ± 50 | 100 ± 50 | 100 ± 20 | 100 ± 20 |
| α [days] | ≥3 | ≥4 | ≥5 | 7 ± 3 | 6 ± 2 | 6 ± 1 |
| second daily dose [µg] | 200 ± 80 | 200 ± 80 | 200 ± 50 | 200 ± 50 | 200 ± 20 | 200 ± 20 |
| β [days] | ≥3 | ≥4 | ≥5 | 7 ± 3 | 6 ± 2 | 6 ± 1 |
| δ [days] | ≥3 | ≥4 | ≥5 | 7 ± 3 | 6 ± 2 | 6 ± 1 |

|  | $C_1$ | $C_2$ | $C_3$ |
|---|---|---|---|
| first daily dose [µg] | 100 ± 20 | 100 ± 20 | 100 ± 20 |
| α [days] | ≥4 | ≥5 | ≥6 |
| second daily dose [µg] | 200 ± 20 | 200 ± 20 | 200 ± 20 |
| β [days] | ≥4 | ≥5 | ≥6 |

28. The method according to claim 15, wherein the pain is
   acute pain or chronic pain; and/or
   nociceptive pain or neuropathic pain; and/or
   postoperative pain, malignant pain, and/or inflammatory pain.

29. The method according to claim 15, wherein the administration regimen comprises
   (i) a first administration interval, which lasts for at least 4 consecutive days, wherein a first daily dose of 100 µg of Cebranopadol is orally administered on every day of the first administration interval; and
   (ii) a second administration interval, which lasts for at least 4 consecutive days and directly follows the first administration interval without interruption, wherein a second daily dose of 200 µg of Cebranopadol is orally administered on every day of the second administration interval.

30. The method according to claim 29, further comprising a third administration interval, which lasts for at least 4 consecutive days and directly follows the second administration interval without interruption, wherein a third daily dose of 300 µg of Cebranopadol is orally administered on every day of the third administration interval.

31. The method according to claim 29, wherein each administration interval lasts for at least 5 consecutive days.

32. The method according to claim 15, wherein the administration regimen comprises
   (i) a first administration interval, which lasts for at least 4 consecutive days, wherein a first daily dose of 100 µg of Cebranopadol is orally administered on every day of the first administration interval; and
   (ii) a second administration interval, which lasts for at least 4 consecutive days and directly follows the first administration interval without interruption, wherein a second daily dose of 300 µg of Cebranopadol is orally administered on every day of the second administration interval.

33. The method according to claim 32, further comprising a third administration interval, which lasts for at least 4 consecutive days and directly follows the second administration interval without interruption, wherein a third daily dose of 400 µg of Cebranopadol is orally administered on every day of the third administration interval.

34. The method according to claim 32, wherein each administration interval lasts for at least 5 consecutive days.

35. A method of reducing side effects associated with treatment for pain, said method comprising administering Cebranopadol according to an administration regimen comprising:
   (i) a first administration interval, which lasts for at least 4 consecutive days, wherein a first daily dose of Cebranopadol is administered on every day of the first administration interval;
   (ii) a second administration interval, which lasts for at least 4 consecutive days and directly follows the first administration interval without interruption, wherein a second daily dose of Cebranopadol is administered on every day of the second administration interval; and
   (iii) an optional third administration interval, which lasts for at least 4 consecutive days and directly follows the second administration interval without interruption, wherein a third daily dose of Cebranopadol is administered on every day of the third administration interval;
   wherein the first daily dose of Cebranopadol is lower than the second daily dose of Cebranopadol; and
   wherein the second daily dose of Cebranopadol is lower than the optional third daily dose of Cebranopadol.

36. The method according to claim 35, wherein the first daily dose of Cebranopadol is in an amount that is expected to be subtherapeutic for the patient.

37. The method according to claim 35, wherein
   the first daily dose of Cebranopadol is equal to or less than 100 µg; and/or
   the first administration interval lasts for at least 4 consecutive days.

38. The method according to claim 35, wherein the first daily dose of Cebranopadol is within the range of from 30 to 70 wt.-% of the second daily dose of Cebranopadol.

39. The method according to claim 35, wherein
   the first daily dose of Cebranopadol is within the range of from 60 to 140 µg; and/or
   the second daily dose of Cebranopadol is within the range of from 160 to 240 µg.

40. The method according to claim 35, wherein the first daily dose of Cebranopadol is within the range of from 5 to 45 wt.-% of the third daily dose of Cebranopadol and wherein the second daily dose of Cebranopadol is within the range of from 30 to 70 wt.-% of the third daily dose of Cebranopadol.

41. The method according to claim 35, wherein the third daily dose of Cebranopadol is 95-105 µg greater than the second daily dose of Cebranopadol.

42. The method according to claim 35, wherein
   the first administration interval, the second administration interval, the optional third administration interval, and/or an optional fourth administration interval, and/or an optional fifth administration interval, and/or an optional sixth administration interval, and/or an optional seventh administration interval independently of one another last for 5 to 7 consecutive days.

43. The method according to claim 35, wherein the administration regimen comprises
   (i) a first administration interval, which lasts for at least α consecutive days, wherein a first daily dose of Cebranopadol is orally administered on every day of the first administration interval; and (ii) a second administration interval, which lasts for at least β consecutive days and directly follows the first administration interval without interruption, wherein a second daily dose of Cebranopadol is orally administered on every day of the second administration interval;

and satisfies any of the following requirements $A_2$ to $C_3$:

|  | $A_2$ | $A_{10}$ | $A_{12}$ | $A_{20}$ | $A_{21}$ |
|---|---|---|---|---|---|
| first daily dose [µg] | 100 ± 80 | 100 ± 50 | 100 ± 50 | 100 ± 20 | 100 ± 20 |
| α [days] | ≥4 | ≥5 | 7 ± 3 | 6 ± 2 | 6 ± 1 |
| second daily dose [µg] | 200 ± 80 | 200 ± 50 | 200 ± 50 | 200 ± 20 | 200 ± 20 |
| β [days] | ≥4 | ≥5 | 7 ± 3 | 6 ± 2 | 6 ± 1 |

|  | $B_2$ | $B_{10}$ | $B_{12}$ | $B_{20}$ | $B_{21}$ |
|---|---|---|---|---|---|
| first daily dose [µg] | 100 ± 80 | 100 ± 50 | 100 ± 50 | 100 ± 20 | 100 ± 20 |
| α [days] | ≥4 | ≥5 | 7 ± 3 | 6 ± 2 | 6 ± 1 |
| second daily dose [µg] | 200 ± 80 | 200 ± 50 | 200 ± 50 | 200 ± 20 | 200 ± 20 |
| β [days] | ≥4 | ≥5 | 7 ± 3 | 6 ± 2 | 6 ± 1 |
| δ [days] | ≥4 | ≥5 | 7 ± 3 | 6 ± 2 | 6 ± 1 |

|  | $C_1$ | $C_2$ | $C_3$ |
|---|---|---|---|
| first daily dose [µg] | 100 ± 20 | 100 ± 20 | 100 ± 20 |
| α [days] | ≥4 | ≥5 | ≥6 |
| second daily dose [µg] | 200 ± 20 | 200 ± 20 | 200 ± 20 |
| β [days] | ≥4 | ≥5 | ≥6 |

44. The method according to claim 35, wherein the pain is
 acute pain or chronic pain; and/or
 nociceptive pain or neuropathic pain; and/or
 postoperative pain, malignant pain, and/or inflammatory pain.

45. The method according to claim 35, wherein the administration regimen comprises
 (i) a first administration interval, which lasts for at least 4 consecutive days, wherein a first daily dose of 100 µg of Cebranopadol is orally administered on every day of the first administration interval; and
 (ii) a second administration interval, which lasts for at least 4 consecutive days and directly follows the first administration interval without interruption, wherein a second daily dose of 200 µg of Cebranopadol is orally administered on every day of the second administration interval.

46. The method according to claim 45, further comprising a third administration interval, which lasts for at least 4 consecutive days and directly follows the second administration interval without interruption, wherein a third daily dose of 300 µg of Cebranopadol is orally administered on every day of the third administration interval.

47. The method according to claim 45, wherein each administration interval lasts for at least 5 consecutive days.

48. The method according to claim 35, wherein the administration regimen comprises
 (i) a first administration interval, which lasts for at least 4 consecutive days, wherein a first daily dose of 100 µg of Cebranopadol is orally administered on every day of the first administration interval; and
 (ii) a second administration interval, which lasts for at least 4 consecutive days and directly follows the first administration interval without interruption, wherein a second daily dose of 300 µg of Cebranopadol is orally administered on every day of the second administration interval.

49. The method according to claim 48, further comprising a third administration interval, which lasts for at least 4 consecutive days and directly follows the second administration interval without interruption, wherein a third daily dose of 400 µg of Cebranopadol is orally administered on every day of the third administration interval.

50. The method according to claim 48, wherein each administration interval lasts for at least 5 consecutive days.

* * * * *